(12) United States Patent
Burch et al.

(10) Patent No.: US 12,412,650 B2
(45) Date of Patent: Sep. 9, 2025

(54) SYSTEM AND METHOD FOR USER INTERFACE MANAGEMENT TO PROVIDE AN AUGMENTED REALITY-BASED THERAPEUTIC EXPERIENCE

(71) Applicant: Christiana Care Health System, Inc., Wilmington, DE (US)

(72) Inventors: Catherine Margaret Burch, Bear, DE (US); James Michael Ellison, Wilmington, DE (US); Alexis Celine Ryan, Wilmington, DE (US); Jennifer Czerepak Rittereiser, Wilmington, DE (US); Jason Anthony Mastriana, Newark, DE (US); Erwin Villareal Bautista, Aston, PA (US); Jonathan Michael Meade, Newark, DE (US); John DiGiovanni, Wilmington, DE (US); Kelsey Ann Kosinski, Wilmington, DE (US); Samantha Joy Taylor, Wilmington, DE (US); John Eric Evans, Landenberg, PA (US)

(73) Assignee: CHRISTIANA CARE HEALTH SYSTEM, INC., Wilmington, DE (US)

( * ) Notice: Subject to any disclaimer, the term of this patent is extended or adjusted under 35 U.S.C. 154(b) by 505 days.

(21) Appl. No.: 17/884,920

(22) Filed: Aug. 10, 2022

(65) Prior Publication Data
US 2023/0046250 A1    Feb. 16, 2023

Related U.S. Application Data

(60) Provisional application No. 63/232,338, filed on Aug. 12, 2021.

(51) Int. Cl.
*G16H 20/70* (2018.01)
*G06V 20/20* (2022.01)
(Continued)

(52) U.S. Cl.
CPC ............. *G16H 20/70* (2018.01); *G06V 20/20* (2022.01); *G06V 40/172* (2022.01); *G16H 40/67* (2018.01)

(58) Field of Classification Search
CPC ........ G16H 20/70; G16H 40/67; G06V 20/20; G06V 40/172
(Continued)

(56) References Cited

U.S. PATENT DOCUMENTS

2019/0163975 A1* 5/2019 Desai .................. G06F 16/5838
2020/0234827 A1* 7/2020 Internicola ............. G06F 3/011

OTHER PUBLICATIONS

BPI Master, "Coach Memory 1.0.16," uptodown app store, retrieved Nov. 9, 2022, retrieved from <<https://coach-memory.en.uptodown.com/android#:~:text=Coach%20Memory%20is%20a%20practical,a%20few%20minutes%20each%20day.>>.
(Continued)

*Primary Examiner* — Quang N Vo
(74) *Attorney, Agent, or Firm* — FisherBroyles LLP

(57) ABSTRACT

A computerized system and method for user interface management provides an augmented reality-based experience that delivers real-time visual cues to a cognitively impaired person, that monitors visual recognition performance, and that provides visual recognition training based on observed visual recognition performance. The system uses image/facial recognition to identify persons/places/objects encountered by a person/dementia sufferer and captured by a camera of a computing device, retrieves information associated with identified person/place/object, and displays retrieved information associated with identified person/place/object to the person/dementia sufferer via the device, e.g., in an augmented reality overlay to an image captured by the camera. The information may identify the identified person's relationship with dementia sufferer and other pertinent details. Accordingly, for example, a person with
(Continued)

cognitive impairment can quickly assess who is approaching them, based on facial recognition.

21 Claims, 26 Drawing Sheets

(51) Int. Cl.
*G06V 40/16* (2022.01)
*G16H 40/67* (2018.01)

(58) Field of Classification Search
USPC .......................................................... 382/118
See application file for complete search history.

(56) References Cited

OTHER PUBLICATIONS

Braingle, "Brain Teasers, Riddles, Trivia, Games and more . . . Briangle is a place to solve puzzles, brush up on your trivia, play games and give your brain a workout. Get ready to have your brain tangled!" retrieved Nov. 9, 2022, retrieved from <<https://www.braingle.com/>>.
Campbell, Luke, "Not the Hole Story," Apple App Store, retrieved Nov. 9, 2022, retrieved from <<https://apps.apple.com/us/app/not-the-hole-story/id431455265>>.
Cognifit, "CogniFit—Brain Training, Test, train, improve your mind," Apple App Store, retrieved Nov. 9, 2022, retrieved from <<https://apps.apple.com/app/cognifit-brain-fitness/id528285610>>.
Constant Therapy Health, "Cognitive, language, and speech therapy at home, on your schedule," retrieved Nov. 9, 2022, retrieved from <<https://constanttherapyhealth.com/constant-therapy/>>.
Elevate, Inc., "Elevate—Braining Training, Memory, Math and Word Games," Apple App Store, retrieved Nov. 9, 2022, retrieved from <<https://apps.apple.com/us/app/elevate-brain-training/id875063456?referrer=singular_click_id%3Db58a17de-a4ec-438d-bafc-755e5af16cad>>.
Emory University, "ReliefLink," Apple App Store, retrieved Nov. 9, 2022, retrieved from <<https://apps.apple.com/us/app/relieflink/id721474553>>.
Greymatters, "Reaching Beyond Dementia," 2015, retrieved Nov. 9, 2022, retrieved from <<https://www.greymatterstous.com/>>.
Happify, "Overcome negative thoughts, stress life's challenges!," retrieved Nov. 9, 2022, retrieved from <<https://www.happify.com/>>.
Health Life Labs, "Portrait Health Brain Teasuers: Imrpove Memory and Attention," AppAdvice, retrieved on Nov. 9, 2022, retrieved from <<https://appadvice.com/app/portrait-health-brain-teasers/371242257>>.
Larrabee GJ, Crook TH. "Estimated prevalence of age-associated memory impairment derived from standardized tests of memory function." Intl Psychogeriatr. 1994;6:95-104.
Lumosity, "Brain training built on science," retrieved Nov. 9, 2022, retrieved from <<https://www.lumosity.com/en/science/>>.
Meternally, retrieved Nov. 9, 2022, retrieved from <<https://meternally.com/>>.

Microsoft Capture Faces dated Aug. 31, 2017, "Vision Framwork in Xamarin.iOS," retrieved from <<https://docs.microsoft.com/en-us/xamarin/ios/platform/introduction-to-ios11/vision>>, retrieved on Sep. 15, 2021.
Mindmate, "MindMate is a reasearch-based platform!" retrieved Nov. 9, 2022, retrieved from <<https://www.mindmate-app.com/science>>.
Mindsparke, "MindSpark's Brain Fitness Training," retrieved on Nov. 9, 2022, retrieved from <<https://www.mindsparke.com/brain_fitness_training.php>>.
Mindware Consulting, Inc.,"Mind Games," Google Play Store, retrieved Nov. 9, 2022, retrieved from <<https://play.google.com/store/apps/details?id=mindware.mindgames&hl=en_US&gl=US>>.
Mochibits, LLC, "Brain Games—Left vs Right," Apple App Store, retrieved Nov. 9, 2022, retrieved from <<https://apps.apple.com/us/app/left-vs-right-brain-games/id576395411>>.
Peak, "The Science Behind Peak," retrieved Nov. 9, 2022, retrieved from <<https://www.peak.net/science/>>.
Personal Zen, "The Science Behind Personal Zen," retrieved Nov. 9, 2022, retrieved from <<https://personalzen.com/science/>>.
Petersen RC, Smith GE, Waring SC, Ivnik RJ, Tangalos EG, Kokmen E. "Mild cognitive impairment: clinical characterization and outcome." Arch Neurol. 1999;56:303-308.
Posit Science Brain HQ, "Why BrainHQ?" retrieved Nov. 9, 2022, retrieved from <<https://www.brainhq.com/why-brainhq/>>.
Sharply Labs, "BrainFox—Braining Training, PLay to improve memory & focus," Apple App Store, retrieved Nov. 9, 2022, retrieved from <<https://apps.apple.com/il/app/brainfox-brain-training/id1492622916>>.
Small GW, Rabins PV, Barry PP, Buckholtz NS, DeKosky ST, Ferris SH, et al. "Diagnosis and treatment of Alzheimer disease and related disorders: consensus statement of the American Association for Geriatric Psychiatry, the Alzheimer's Association, and the American Geriatrics Society. " JAMA. 1997;278:1363-1371.
Tactus Therapy Solutions Ltd, "Category Therapy, Sorting Words by Categories," Apple App Store, retrieved Nov. 9, 2022, retrieved from <<https://apps.apple.com/us/app/category-therapy/id571551926>>.
Tactus Therapy, Bes-Selling Adult Speech Therapy Apps, retrieved Nov. 9, 2022, retrieved from <<tactustherapy.com/apps/>>.
TalkPath Therapy, "TalkPath Therapy:Begin Rebuilding Speech Today," retrieved Nov. 9, 2022, retrieved from <<https://www.aphasia.com/talkpath-therapy-aphasia-app/>>.
Timeless Innovations LLC, Timeess|Care Apple App Store, retrieved Nov. 9, 2022, retrieved from <<https://apps.apple.com/us/app/timeless-care/id1439644684?ign-mpt=uo%3D2>>.
Total Eclipse P.C. "Clockwork Brain Training | Memory & Attention Game," AppAdvice, retrieved Nov. 9, 2022, retrieved from <<https://appadvice.com/app/clockwork-brain-training-memory-attention-game/442745768>>.
Vivity Labs, "Fit Brains Trainer," uptodown app store, retrieved Nov. 9, 2022, retrieved from <<https://fit-brains-trainer.en.uptodown.com/android>>.
Waterfall, Steven, "Eidetic—Spaced Repetition, Learn & remeber anything," Apple App Store, retrieved Nov. 9, 2022, retrieved from <<https://apps.apple.com/us/app/eidetic-spaced-repetition/id536240413>>.

\* cited by examiner

SYSTEM AND METHOD FOR USER INTERFACE MANAGEMENT TO PROVIDE AN AUGMENTED REALITY-BASED THERAPEUTIC EXPERIENCE

CROSS-REFERENCE TO RELATED APPLICATION

This application claims the benefit of priority of U.S. Provisional Patent Application No. 63/232,338, filed Aug. 12, 2021, the entire disclosure of which is hereby incorporated herein by reference.

FIELD OF THE INVENTION

The present invention relates generally to controlling a user interface of a computerized system to provide an augmented-reality-based information display and user experience, and more particularly to providing a display of information on a computerized device that provides an experience delivering real-time visual cues to a cognitively impaired person, and that provides a performance-based therapeutic experience for mitigating the cognitive impairment.

DISCUSSION OF RELATED ART

Many Americans and others suffer from a form of cognitive impairment, often referred to as dementia, which is a broad term often used to describe a range of cognitive impairment symptoms or conditions, including Alzheimer's disease, vascular degeneration, Lewy body formation, and frontotemporal degeneration. Generally, such dementia is caused by abnormal brain changes that trigger a decline in the ability to think clearly. By certain estimates, approximately 6.2 million Americans, or approximately one in nine people, age 65 and older, are living with Alzheimer's dementia in 2021. As American population ages, the number of new and existing cases of Alzheimer's disease is expected to increase.

The costs of health care and long-term care for individuals living with Alzheimer's or other dementias are substantial, and dementia is one of the costliest conditions to society. In 2021, Alzheimer's and other dementias are expected to cost the nation approximately $355 billion, including $239 billion in Medicare and Medicaid payments combined. Without a treatment to slow, stop, or prevent the disease, it is estimated that, in 2050, Alzheimer's will cost more than $1.1 trillion (in 2021 dollars). This dramatic rise includes more than three-fold increases both in government spending under Medicare and Medicaid and in out-of-pocket spending.

Dementia impairs the quality of life of the dementia sufferer, and his or her loved ones. Additionally, it compromises the ability of the dementia sufferer to provide adequate self-care, or to receive home health care or other healthcare services. For example, loss of the ability to recognize the faces of loved ones, caregivers and other people known to the dementia suffer is common. This can be dangerous in a home health care context. For example, a failure to recognize the intimate partner/caregiver may threaten the safety of the partner/caregiver and undermine the partner/caregiver's ability to continue to provide safe and effective care in a home environment. Solutions that mitigate dementia symptoms are uplifting to the mood of the dementia sufferer and of caregivers, and can desirably prolong the duration of successful home care, prior to transfer to a long-term care institution.

To some extent, cognitive impairment may be reversable and/or treatable, to improve the degree of impairment. For some people, cognitive impairment can be lessened, or at least current brain function may be maintained, by performance of certain activities, such as those that improve visual recognition and recall.

What is needed is a computerized system and method providing for user interface management to provide an augmented-reality-based information display that provides an experience delivering real-time visual cues to a cognitively impaired person, and that mitigates cognitive impairment conditions by promoting visual recognition, to build and/or maintain trust in in-home visitors, and that supports dementia sufferers in living at home successfully and safely.

SUMMARY

The present invention provides a computerized system and method for user interface management that provides an augmented reality-based experience that delivers real-time visual cues to a cognitively impaired person, that monitors visual recognition performance, and that provides visual recognition training based on observed visual recognition performance. More particularly, the system uses image/facial recognition to identify persons/places/objects encountered by a person/dementia sufferer and captured by a camera of a computing device, retrieves information associated with identified person/place/object, and displays retrieved information associated with identified person/place/object to the person/dementia sufferer via the device, e.g., in an augmented reality overlay to an image captured by the camera. The information may identify the identified person's relationship with dementia sufferer and other pertinent details. Accordingly, for example, a person with cognitive impairment can quickly assess who is approaching them, based on facial recognition.

BRIEF DESCRIPTION OF THE FIGURES

For a better understanding of the present invention, reference may be made to the accompanying drawings in which:

FIGS. 4-25 illustrate exemplary graphical user interface windows displayable by the exemplary special-purpose Augmented Reality-Based Monitoring Device in accordance with an exemplary embodiment of the present invention.

DETAILED DESCRIPTION

Figure 1A:
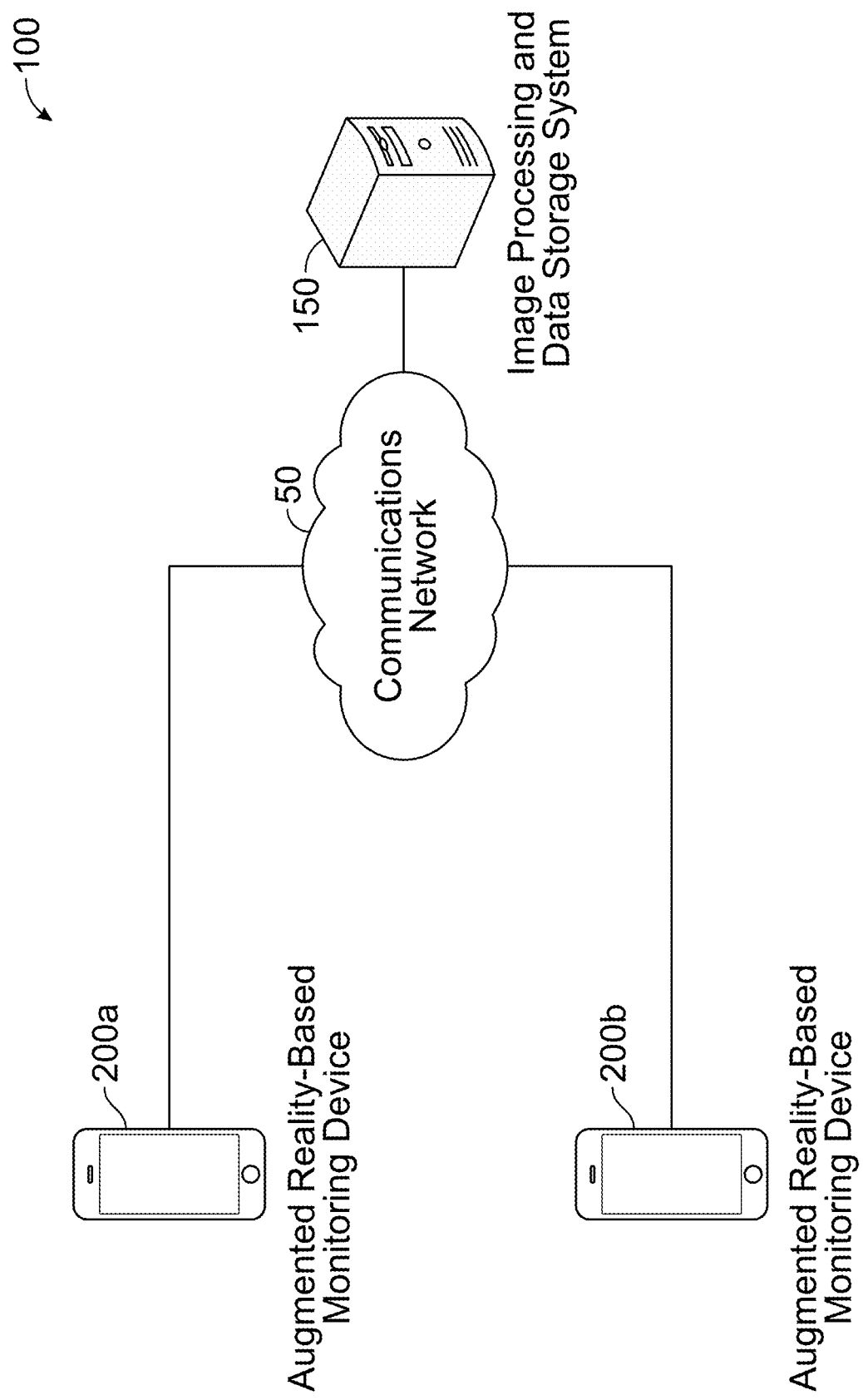
FIGS. 1A and 1B are system diagrams showing an exemplary network computing environment in which the present invention may be employed.

According to illustrative embodiment(s) of the present invention, various views are illustrated in FIGS. 1A-25 and like reference numerals are used consistently throughout to refer to like and corresponding parts of the invention for all of the various views and figures of the drawings.

The following detailed description of the invention contains many specifics for the purpose of illustration. Any one of ordinary skill in the art will appreciate that many variations and alterations to the following details are within scope of the invention. Accordingly, the following implementations of the invention are set forth without any loss of generality to, and without imposing limitations upon, the claimed invention.

System Environment

Figure 1B:
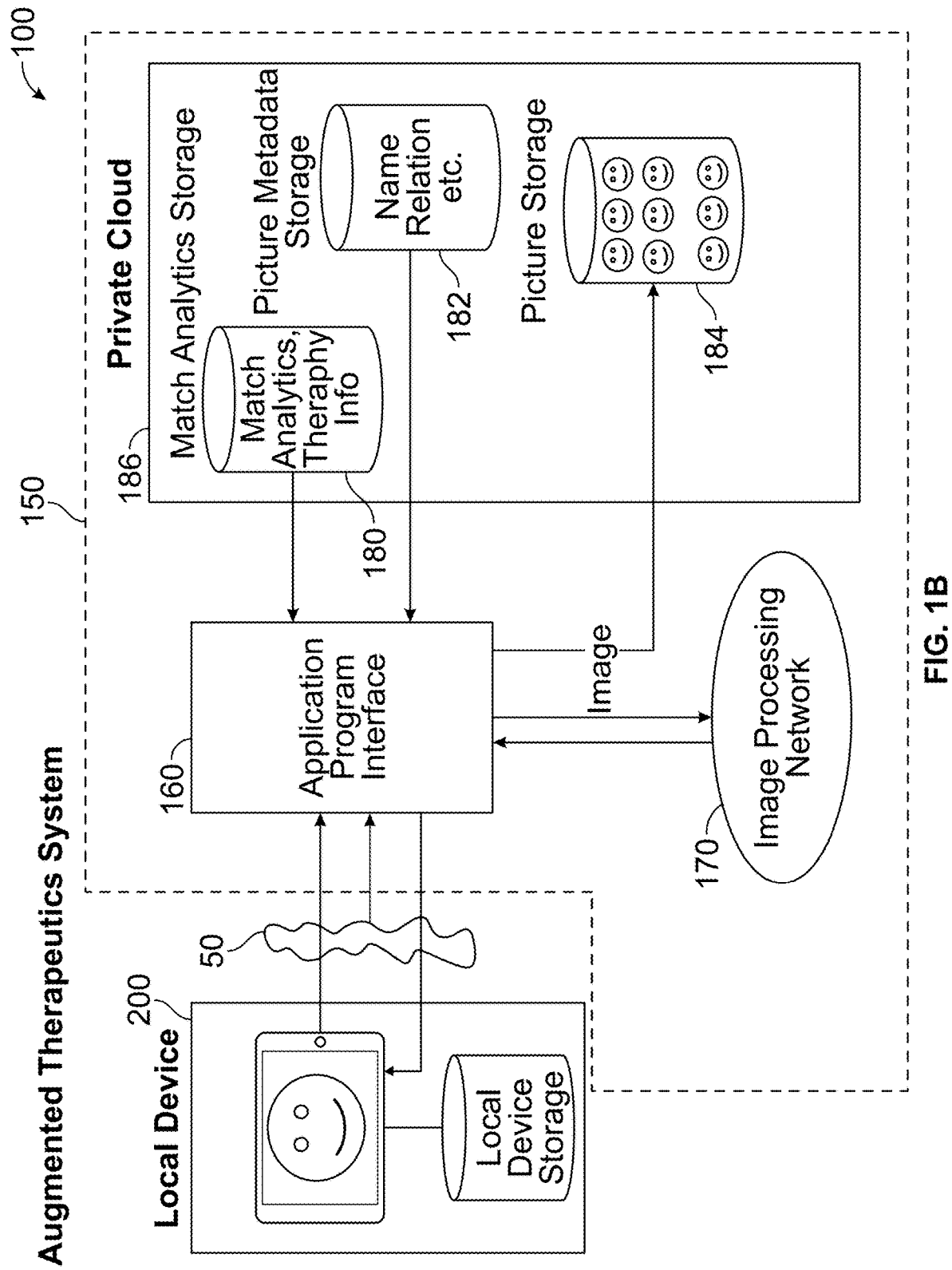

An exemplary embodiment of the present invention is discussed below for illustrative purposes. FIGS. 1A and 1B are system diagrams showing an exemplary network computing environment 100 in which the present invention may be employed. As shown in FIGS. 1A and 1B, the exemplary network environment 100 includes conventional computing hardware and software for communicating via a communications network 50, such as the Internet, etc., using Augmented Reality-Based Monitoring Devices (ARBMD) 200*a*, 200*b*, each of which may be, for example, one or more personal computers/PCs, laptop computers, tablet computers, smartphones, or other computing device hardware.

In accordance with a certain aspect of the present invention, one or more of the Augmented Reality-Based Monitoring Devices 200*a*, 200*b* may store and execute an "app" or other purpose-specific application software in accordance with the present invention, although this is not required in all embodiments. In other embodiments, a SaaS or internet/web-based software platform may be used to deliver similar functionality to the ARMBDs 200*a*, 200*b*.

In accordance with the present invention, the network computing environment 100 further includes an Image Processing and Data Storage System (IPADSS) 150. In this exemplary embodiment, the IPADSS 150 is operatively connected to the Augmented Reality-Based Monitoring Devices 200*a*, 200*b* for data communication via the communications network 50. The IPADSS 150 is operable to receive image data, to process that image data to perform an image recognition (e.g., facial recognition) function to identify a person, place, objects, etc., e.g., by comparing the received image data to stored image data for known persons, places, objects, etc., and to return results in the form of data identifying and/or related the associated person, place, object, etc. For example, the IPADSS 150 may receive photographic or videographic image data, or other data or inputs, from each Augmented Reality-Based Monitoring Devices 200*a*, 200*b* by data communication via the communications network 50. Hardware and software for enabling communication of data by such devices via such communications networks are well known in the art and beyond the scope of the present invention, and thus are not discussed in detail herein.

In certain embodiments, the IPADSS 150 may be implemented as a cloud-based service configured to receive data via an application program interface (API), process the image data to produce results in accordance with the present invention, and to return results in the form of data to the Augmented Reality-Based Monitoring Devices 200*a*, 200*b*. The IPADSS 150 may be implemented in part using a commercially-available internet cloud-based image processing and data storage service. For example, the commercially available Amazon Rekognition software/system/service provided by Amazon Web Services, Inc. of Seattle, Washington may be leveraged to provide a portion of the functionality of the IPADSS 150 using its existing commercially-available CompareFaces API to compare a device-captured image with a set of known/previously-stored images on a per-user basis. The commercially-available Rekognition software/system/service provides a result set that orders/ranks known images by similarity level to the captured image that was submitted via the CompareFaces API, as known in the art. It should be noted that in FIG. 1B, the Image Processing Network 170 may be implemented using the commercially-available Rekognition and Compare Faces software/system/functionality, and that the API 160 shown in FIG. 1B provides novel functionality in accordance with the present invention, including interfacing with Match Analytics data store 180, Picture Metadata Storage 182 (data about how the image relates to the patient, such as patient name, list of names the patient knowns, relationships, list of places known to the patient, etc.) and Picture Storage data store 184, which may be stored in a private data cloud 186. Further, the novel API 160 in accordance with present invention makes calls to implement certain business logic functionality in accordance with the present invention, e.g., to make use of the commercially-available Facial Rekognition service and CompareFaces API to determine a face match, etc. in accordance with the present invention.

In accordance with an exemplary embodiment of the present invention, the provided result set is processed to compare the record of the result set that has the highest similarity-level against a chosen similarity threshold to determine if it should be determined that the images match, such that the previously-stored matching image identified can be used to identify the subject of the new camera-captured image. If it is determined that the similarity threshold has been exceeded, then it is determined that the images match, and information associated with the subject of the matching images (particularly, the previously-stored image) is retrieved and displayed to the user via the device's graphical user interface. Alternatively, if the record of the result set having the highest similarity level/ranking is below the similarity threshold, then information associated with other known persons/previously-stored images are retrieved and displayed to the user via the device's graphical user interface.

Accordingly, the capture of images with a camera of a smartphone or other computing device, the use of machine learning or other techniques to process multiple images of a known person, etc. to "train" the image recognition system, and the use of artificial intelligence to match a new captured image to a stored image of a known person, etc. may be performed in a conventional manner known in the art, and thus are outside the scope of the present invention. Accordingly, these aspects are not discussed in greater detail herein. The capture and storage of images for image recognition system training may be performed as a preliminary step to use of the system as described herein, in a separate but conventional process.

Augmented Reality-Based Monitoring Device

Figure 2:
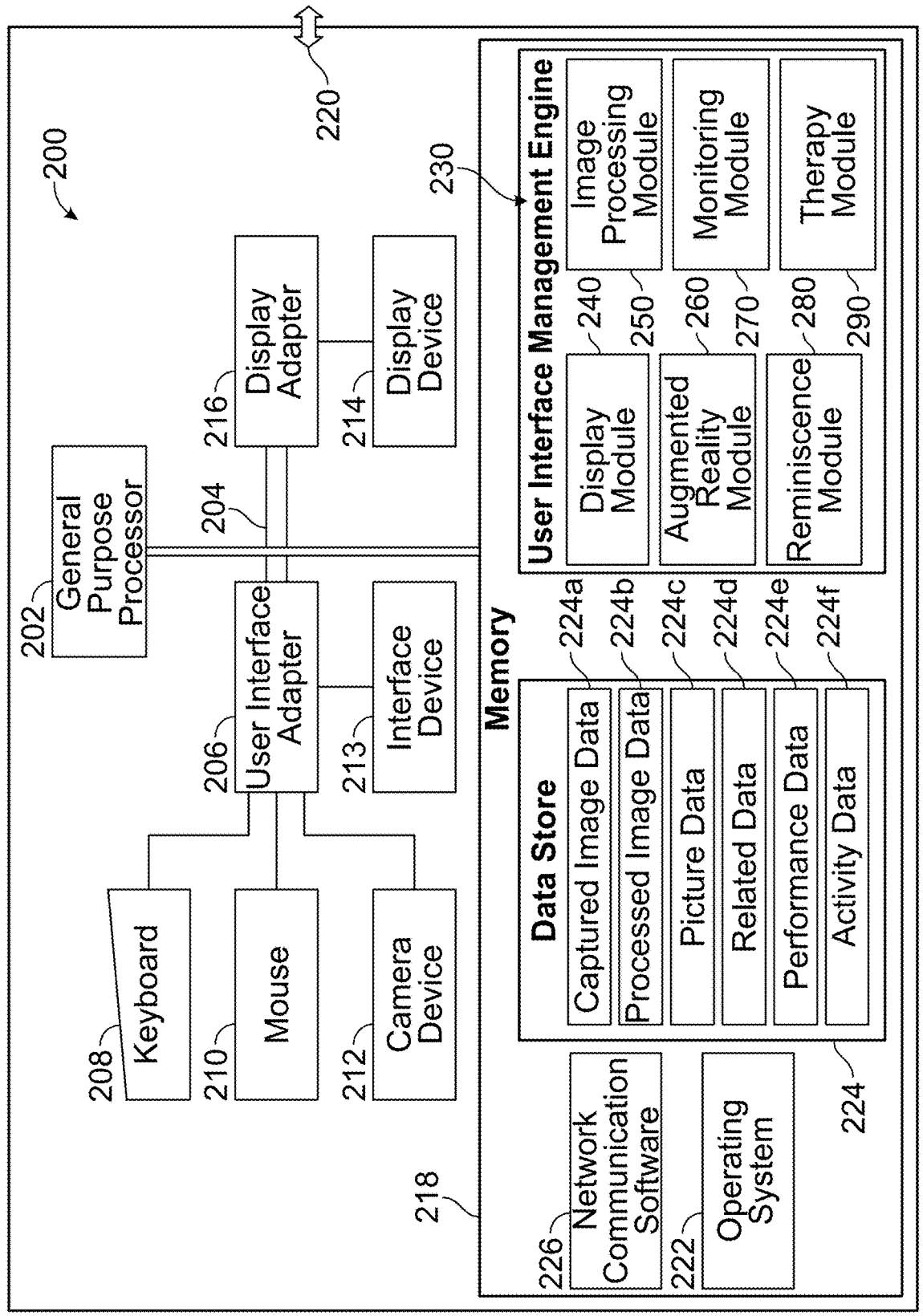
FIG. 2 is a schematic diagram of an exemplary special-purpose Augmented Reality-Based Monitoring device in accordance with an exemplary embodiment of the present invention.

FIG. 2 is a block diagram showing an exemplary Augmented Reality-Based Monitoring Device (ARMBD) 200 in accordance with an exemplary embodiment of the present invention. The ARMBD 200 is a special-purpose computer system that includes conventional computing hardware storing and executing both conventional software enabling operation of a general-purpose computing system, such as operating system software 222, network communications software 226, and specially-configured computer software for configuring the general-purpose hardware as a special-purpose computer system for carrying out at least one method in accordance with the present invention. By way of example, the communications software 226 may include conventional web server software, and the operating system software 22 may include iOS, Android, Windows, Linux software.

Accordingly, the exemplary ARMBD 200 of FIG. 2 includes a general-purpose processor, such as a microprocessor (CPU), 102 and a bus 204 employed to connect and enable communication between the processor 202 and the components of the presentation system in accordance with known techniques. The exemplary presentation system 200 includes a user interface adapter 206, which connects the processor 202 via the bus 204 to one or more interface devices, such as a keyboard 208, mouse 210, camera/imaging device 212, and/or other interface devices 213, which can be any user interface device, such as a microphone, touch sensitive screen, digitized entry pad, etc. The bus 204 also connects a display device 214, such as an LCD screen or monitor, to the processor 202 via a display adapter 216. The bus 204 also connects the processor 202 to memory 218, which can include a hard drive, diskette drive, tape drive, etc.

The ARMBD 200 may communicate with other computers or networks of computers, for example via a communications channel, network card or modem 220. The ARMBD 200 may be associated with such other computers in a local area network (LAN) or a wide area network (WAN). Such configurations, as well as the appropriate communications hardware and software, are known in the art.

The ARMBD 200 is specially-configured in accordance with the present invention. Accordingly, as shown in FIG. 2, the ARMBD 200 includes computer-readable, processor-executable instructions stored in the memory 218 for carrying out the methods described herein. Further, the memory 218 stores certain data, e.g., in one or more databases or other data stores 224 shown logically in FIG. 2 for illustrative purposes, without regard to any particular embodiment in one or more hardware or software components.

Further, as will be noted from FIG. 2, the ARMBD 200 includes, in accordance with the present invention, a User Interface Management Engine (UIME) 230, shown schematically as stored in the memory 218, which includes a number of additional modules providing functionality in accordance with the present invention, as discussed in greater detail below. These modules may be implemented primarily by specially-configured software including microprocessor—executable instructions stored in the memory 218 of the ARMBD 200. Optionally, other software may be stored in the memory 218 and and/or other data may be stored in the data store 224 or memory 218.

As shown in FIG. 2, the exemplary embodiment of the ARMBD 200 also includes a Display Module (DM) 240. The DM 240 is responsible for causing display of graphical user interface windows at the ARMBD 200 and for receiving user inputs via the ARMBD 200.

For example, the DM 240 may cause display of graphical user interface windows prompting a dementia sufferer, on-site healthcare provider or other person to capture images as part of an initial image recognition training process, and/or offering user-selectable options for navigating a user interface in accordance with the present invention, as will be appreciated from FIGS. 4-25. Accordingly, users can interact with the ARMBD 200 and its user interface in accordance with the present invention, e.g., to select user-selectable options, e.g., to perform image recognition tasks and/or to perform therapeutic activities designed to help mitigate dementia.

In accordance with the present invention, the exemplary embodiment of the ARMBD 200 shown in FIG. 2 also includes an Image Processing Module (IPM) 250. The IPM 250 is responsible for control of the camera of the ARMBD 200 to capture photographic and/or videographic images, e.g., in response to a user's selection of an option to initiate an image recognition task, and for performance of the image process, e.g., facial recognition or recognition of places, objects, etc., for the purpose of the present invention. Although in some embodiments this task may be performed at the ARMBD 200, in this embodiment, this task is performed outside the ARMBD 200, namely, by a cloud-based service and associated hardware. Accordingly, in this embodiment, the IPM 250 is responsible for transmitting image data via the network 50 to the Image Processing and Data Storage System 250, so that the IPADSS 150 can perform the image recognition task to identify an image subject (e.g., person, place, object, etc.) before returning results to the ARMBD 200. The IPM 250 may also store the raw image captured by the camera as Captured Image Data 224a in the data store 224, and store Processed Image Data 224b in the data store 224, which in this example, may be data received from the IPADSS 150 via the network 50 as a result of the image recognition task performed by the IPADSS 150.

The IPM 250 may also be responsible for retrieving additional images/pictures that relate/correspond to the subject as identified by the Processed Image Data 224a and for storing those additional images/pictures in the Picture Data 224c in the Data Store 224. For example, if the Processed Image Data results in identifying a subject of the image as the face of a known person, the IPM 250 may retrieve additional pictures of that same known person. The IPM 250 may also be responsible for retrieving additional contextual information relating/corresponding to the subject, and storing the additional contextual information as Related Data 224d in the data store 224. For example, if the processed image data results in identifying the subject of the image as the face of a known person, the IPM 250 may retrieve additional information such as the name, relationship, activity and/or other contextual information for that same known person.

Figure 6:
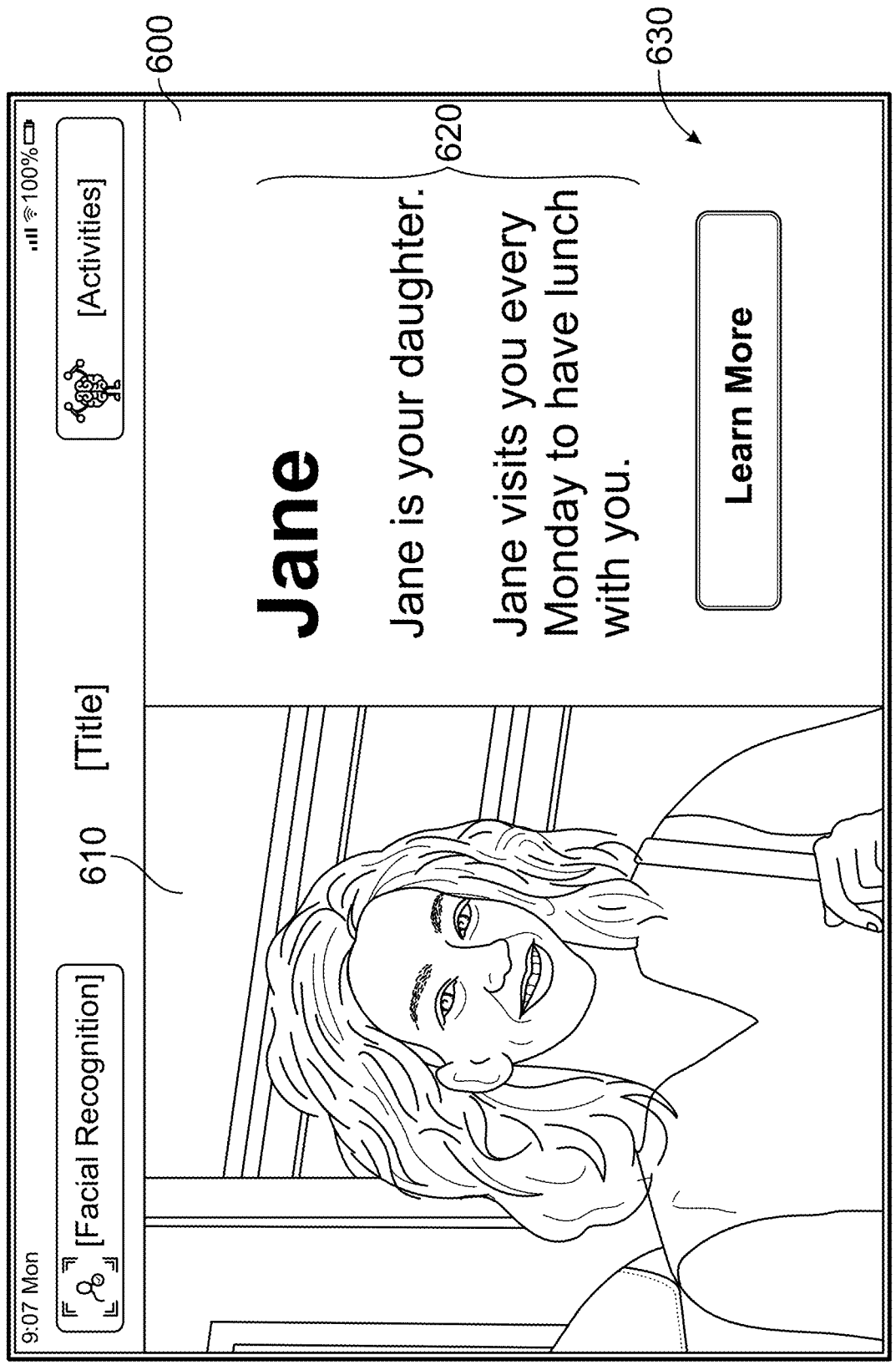

In accordance with the present invention, the exemplary embodiment of the ARMBD 200 shown in FIG. 2 also includes an Augmented Reality Module (ARM) 260. The ARM 260 is responsible for displaying via the ARMBD 200 display device 214 relevant picture and/or contextual information relating to the subject identified by the IPM 250. The relevant picture and/or contextual information associated with the subject of the image may be retrieved from the Picture Data 224c and/or the Related Data 224d. Preferably, the ARM 260 displays the relevant picture and/or contextual information in an augmented reality-type display in which the relevant picture and/or contextual information is displayed on a display 214 of the ARMBD 200 concurrently with, e.g., alongside or in superposition, a still or video image captured in real time by the camera 212 of the ARMBD 200 and displayed on the display device 214 of the ARMBD 200. By way of example, the augmented reality-type display may be provided in the form of an overlay to a photographic and/or videographic image capture by the camera device 212, e.g., with either a transparent or opaque background, e.g., as shown in FIG. 6.

Further, in accordance with the present invention, the exemplary embodiment of the ARMBD 200 shown in FIG. 2 also includes a Monitoring Module (MM) 270. The MM 270 is responsible for monitoring the user's interaction with the ARMBD 200 to identify persons, places, objects, etc. and store data indicating subjects that the user is having difficulty in recognizing. The MM 270 does so, at least in part, by tracking the subjects (persons, places, objects, etc.) identified by the IPM 250. More particularly, it is contemplated that to the extent a person with dementia recognizes a subject, he or she will not use the ARMBD 200 to identify the subject and provide helpful information associated with subject. Accordingly, to the extent that a person with dementia uses the ARMBD 200 to identify a subject and provide helpful information, that is taken to be an indication that the person with dementia is having difficulty/failing to recognize that subject without assistance. The MM 270 may also identify errors in making correct identifications during therapy activities and store data indicating subjects that the user is having difficulty in recognizing. The MM 270 stores data indicating the subjects that the user is having difficulty in recognizing in the data store 224 as Performance Data 224e. This information may be used to customize therapy activities to focus more heavily, e.g., in a proportion greater than a proportion resulting from an equal and/or random distribution, on activities designed to promote recognition of the particular subjects identified in the Performance Data 224e.

Further still, in accordance with the present invention, the exemplary embodiment of the ARMBD 200 shown in FIG. 2 also includes a Reminiscence Module (RM) 280. The RM 280 is responsible for displaying via the ARMBD 200 stored images of persons, places, objects, etc. that are known (and should be recognizable to) the dementia sufferer. This is somewhat analogous to browsing an album of personal photographs of the dementia sufferer, and may be an activity that the dementia sufferer and a caregiver could engage in together, with the dementia sufferer browsing the photos, sharing recollections, and listening to recollections offered by the caregiver, all of which is designed to stimulate recognition and recall on the part of the dementia sufferer, and intended to improve cognitive function. The RM 280 may be configured to retrieve images and/or related data from Picture Data 224c and Related Data 224d, and display them in sequential or random order. Alternatively, the order and/or frequency of display of subjects may be influenced by the Performance Data, so that subjects that are more difficult to recognize and displayed with a relatively greater frequency, etc.

Still further, in accordance with the present invention, the exemplary embodiment of the ARMBD 200 shown in FIG. 2 also includes a Therapy Module (TM) 290. The TM 290 is responsible for displaying via the display device 214 of the ARMBD 200 user interface windows providing the dementia sufferer with activities, such as "brain games," that are designed to stimulate recall and recognition on the part of the dementia sufferer, to improve cognitive function, e.g., based on the Performance Data 224e indicating recall difficulties. Any suitable activity may be employed, but in a preferred embodiment, the activities call for use of recall and recognition skills in relation to images of subjects and/or associated information, such as related images retrieved from Picture Data 224c and/or related contextual information retrieved from Related Data 224d. In certain embodiments, the TM 290 is configured to reference the Performance Data 224e to identify certain subjects that the dementia sufferer is having difficulty recognizing, and to configure the activities to place a greater emphasis on recall and recognition of those same subjects, to improve cognitive function. This may involve selecting those subjects as part of a subset of subjects to be displayed during an activity and/or displaying those subjects with a greater frequency and/or higher rate than other subjects throughout one or more activities.

Figure 3:
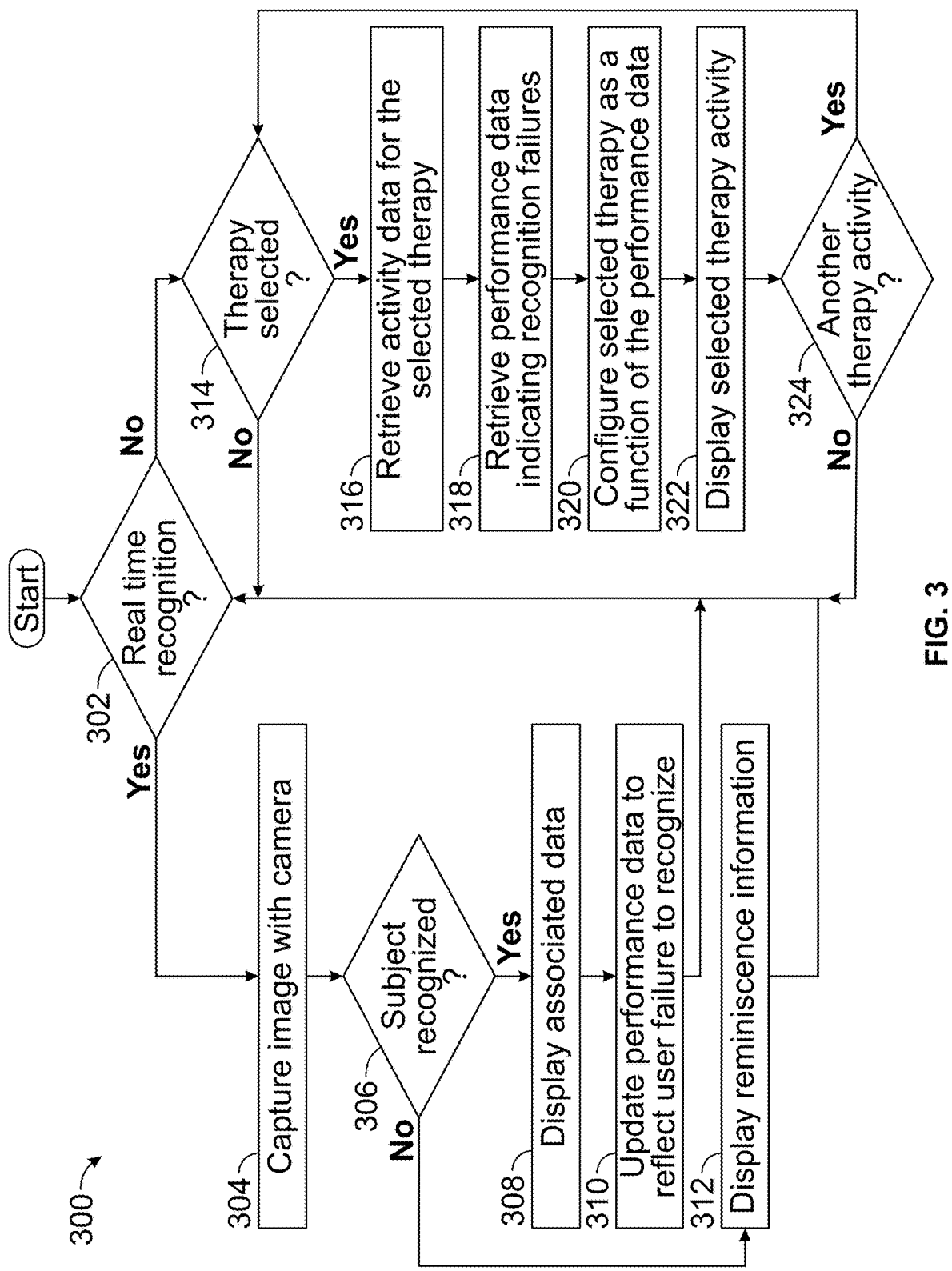
FIG. 3 is a flow diagram illustrating an exemplary method for user interface management to provide an augmented reality-based therapeutic experience in accordance with an exemplary embodiment of the present invention.

FIG. 3 shows a flow diagram 300 illustrating an exemplary method for user interface management, carried out by the ARMBD 200, to provide an augmented-reality-based information display and user experience, and more particularly to providing a display of information on a computerized device that provides an experience delivering real-time visual cues to a cognitively impaired person, and that provides a performance-based therapeutic experience for mitigating the cognitive impairment. Accordingly, the method provides an augmented reality-based therapeutic experience in accordance with an exemplary embodiment of the present invention.

Referring now to FIG. 3, the exemplary method begins with the determination of whether the user of the ARMBD 200 (e.g., dementia sufferer) has selected to perform real time recognition of a subject, e.g., of a face of a person in proximity of the user or a printed photograph of a subject, as shown at 302. This may be determined by the user's selection of a user selectable button 402 displayed as part of a graphical user interface window 400 displayed on the display device 214 of the ARMB200 by the Display Module 240, as shown in FIG. 4.

Figure 4:
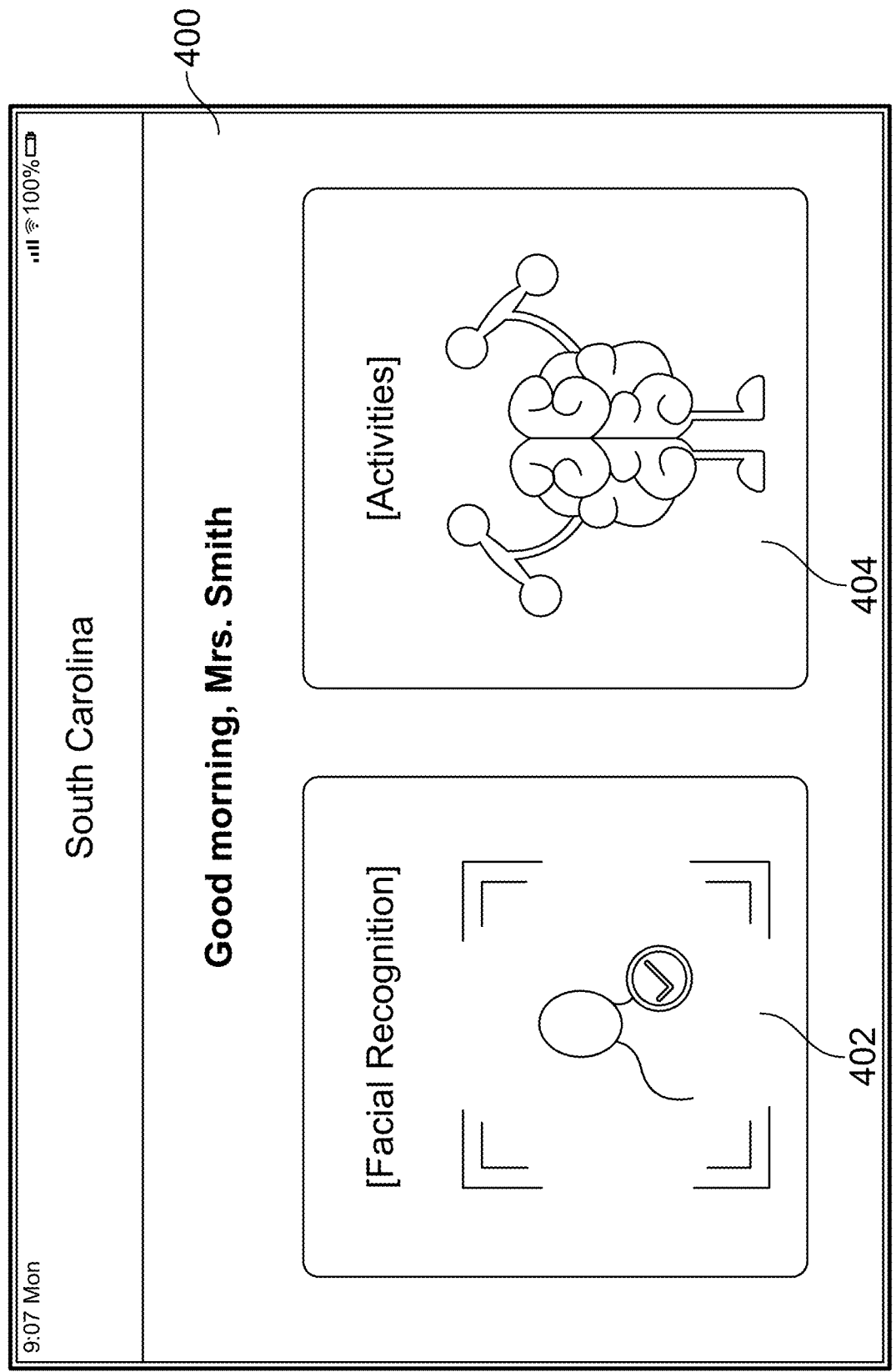
Figure 5:
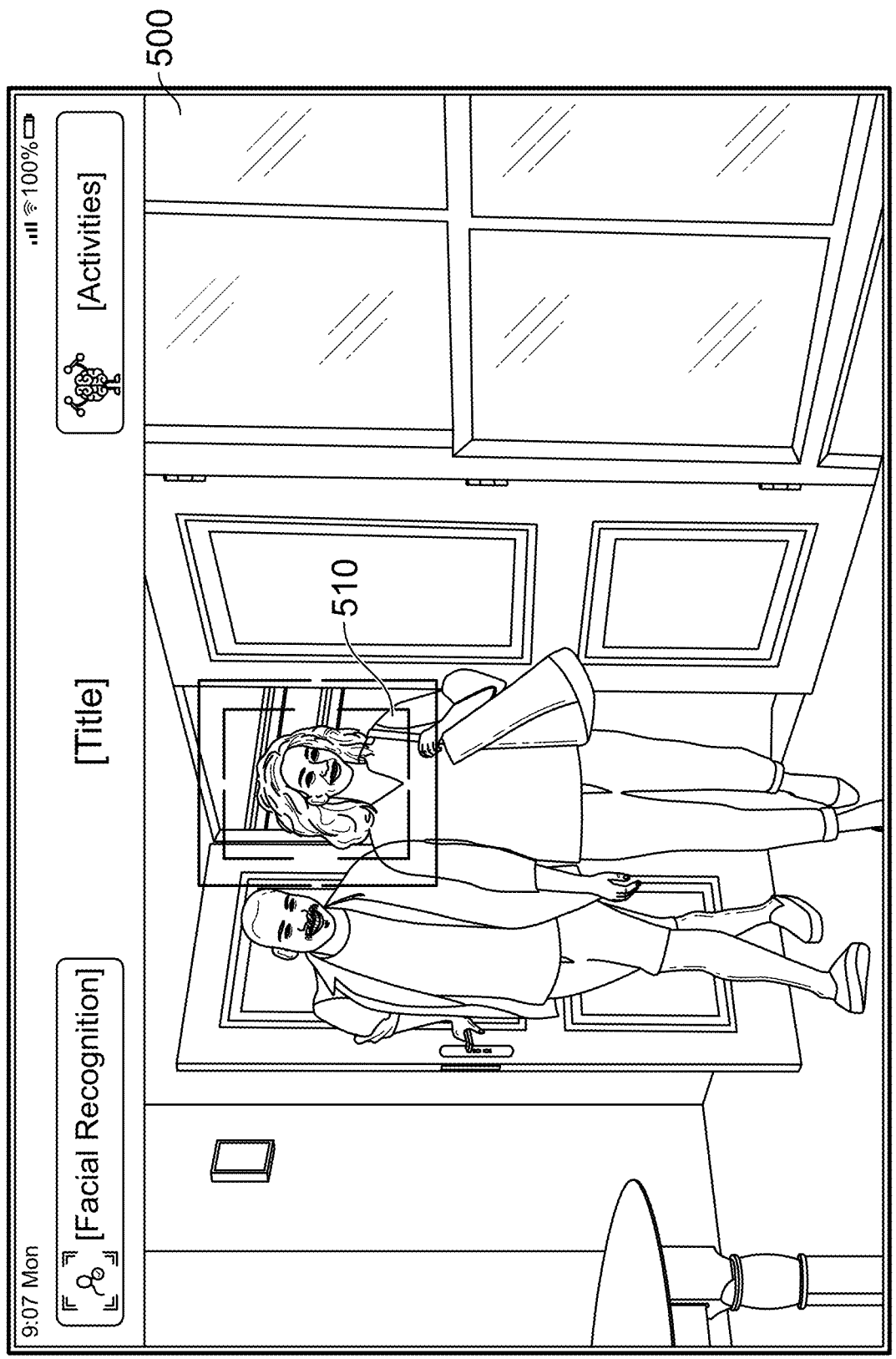

Upon selection of the user selectable button 402 displayed in FIG. 4, the IPM 250 causes the camera device 212 of the ARMBD 200 to operate and capture an image of the ambient environment, as shown at 304, as will be appreciated from graphical user interface window 500 of FIG. 5, showing a real-time image captured by the camera 212. In accordance with the present invention, and in contrast to prior art techniques, the IPM 250 may be configured for recognition purposes to process only a most prominent face in the image, as shown by the overlay of brackets 510 around the most prominent face shown in the window 500 of FIG. 5. For example, this may be achieved in accordance with the present invention by using a CaptureFaces API and/or functionality that is commercially-available from Microsoft Corporation of Redmond, Washington to detect every face in the captured image, and then, in accordance with the present invention, by calculating the width and height of all captured faces, and comparing the faces to identify the largest face, and using the largest face as the most prominent face for performance of matching, etc. only with respect to the face determined to be the largest, and thus most prominent, face in the captured image. The software and/or functionality for identifying the largest/most prominent face from all faces detected by conventional face identification software may be provided in accordance with the present invention by software resident on the ARMBD 200. The captured image data, and any associated metadata, then cause to be stored as Captured Image Data 224a, and to perform a recognition task to identify a subject in the image, which in this example, involves transmission of associated captured image data to the IPADSS 150.

The captured image data is then processed for subject recognition purposes, e.g., by the IPADSS 150, which may involve use of known artificial intelligence techniques to compare the captured image to one or more previously stored images associated with one or more known subjects, and stored with the IPADSS 150 or otherwise to be accessible to the IPADSS 150 or recognition process. The IPADSS 150 then transmits the results of its analysis, which may involve identification of a particular known subject, or a failure to recognize a particular known subject, via the network 50, in this example, to the ARMBD 200.

If it is determined at 306 that a known subject was recognized, e.g., as a particular person, then the ARM 260 displays associated picture and/or related data relating to the identified subject via the display device 214 of the ARMBD 200, as shown at 308. This may involve the IPM 250's retrieval from storage of Picture Data 224c, such as other photographic images of the same subject, and/or Related Data 224d, such as relationship, role, or other contextual information relating to the same subject, from data storage for known subjects, from the data store 224 of the ARMBD 200. Such picture data and related data may be provided as part of a configuration step prior to performance of this method. In this example, such photographic images and related data are stored at the IPADSS 150, although will be appreciated that this information could alternatively be stored locally on the ARMBD 200 or elsewhere. Picture data and related data received from the IPADSS 150 is stored in the data store 224 as Picture Data 224c and Related Data 224d, respectively. The relevant Picture Data 224c and/or Related Data 224d is preferably displayed in an augmented reality-type display of a graphical user interface window such as window 600 shown in FIG. 6, which includes a portion of the image (still or video) captured by the camera 610, and an overlay of text 620 on an opaque background 630 showing retrieved related data corresponding to the subject shown in the image and recognized/identified by the IPM 250.

Accordingly, it will be appreciated that this information, displayed to the user via the ARMBD 200 in real-time (while a person, place, object is near the user) is helpful to the user who may not recognize the person, for example, present in the proximity of the user. For example, the device may remind the user that the person present is a caregiver, a relative, or a friend, so that the user may act accordingly.

As referred to above, the Monitoring Module 270 monitors use of the ARMBD 200 and acknowledges that the user has used the ARMBD 200 to generate an assistive display helpful in recognizing the particular subject identified in that image by the IPM 250, and accordingly, the MM 270 updates the Performance Data 224e, by storing data as Performance Data 224e in the data store 224, to reflect that the user has had difficulty in, e.g. has failed, to recognize that particular subject, as shown at 310 in FIG. 3. The method flow then returns to a determination of whether a subsequent real-time recognition task is desired to be performed, as shown at 302. Accordingly, for example, the Display Module 240 may again display the graphical user interface window 400 of FIG. 4, which displays the user selectable button 402 for again performing an image recognition task.

Figure 7:
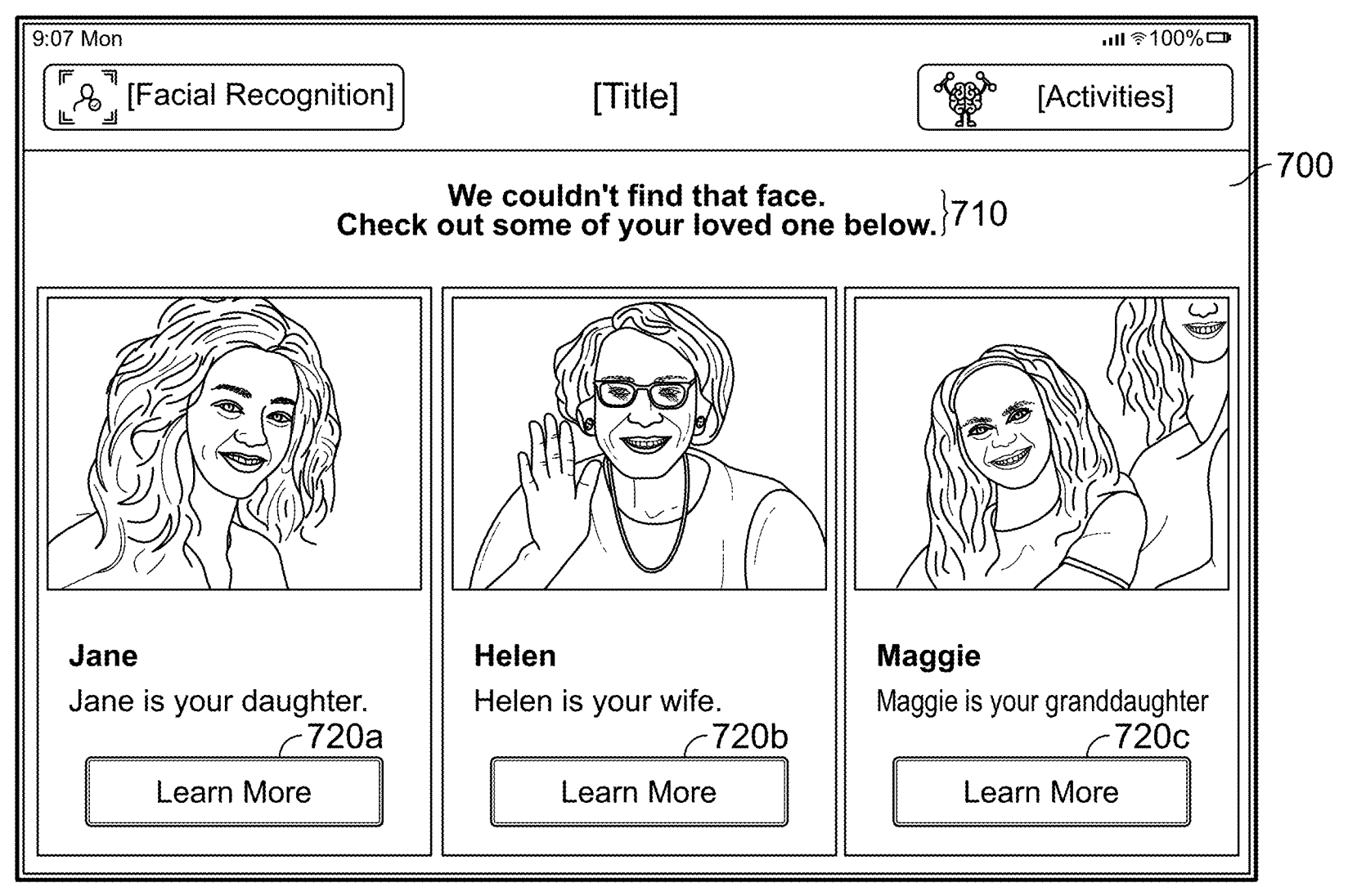
Figure 8:
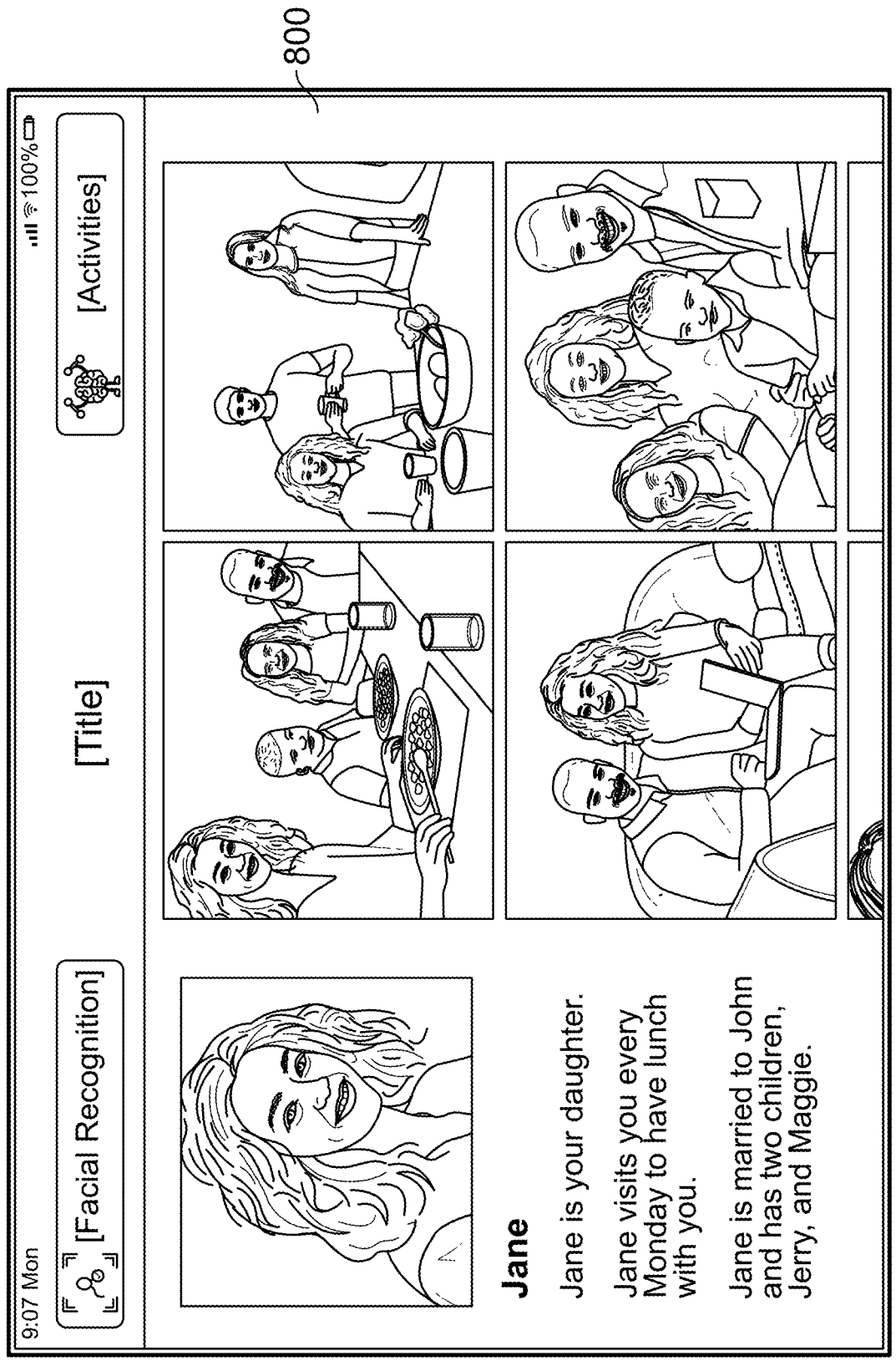

If, however, it is determined at 306 that the subject was not recognized by the IPM 250, e.g., because there are no stored pictures of the subject of the captured image for comparison purposes, then the image recognition has failed, or the subject is not known to the user, or the system has not been configured to recognize that subject. In this exemplary embodiment, the method proceeds to display reminiscence information, as shown at 312 of FIG. 3. For example, the Reminiscence Module 280 may cause display of a graphical user interface window 700, as shown in FIG. 7, that displays a textual or other indication 710 that the subject of the captured image was not identified, and displays one or more user selectable buttons 720a, 720b, 720c that the user may select to browse images and/or related contextual information associated with a person that is known to the user, and for which picture data and related data are stored by the system. This information may be retrieved from Picture Data 224c and/or Related Data 224d at the ARMBD 200 and/or from the IPADSS 150. In response to selection of one of those buttons, e.g., button 720a of FIG. 7, the Reminiscence Module 280 retrieves relevant picture data and/or related data and displays it by a graphical user interface window, such as window 800 shown in FIG. 8, that includes one or more images and or related contextual data, as shown in FIG. 8. As referred to above, this can be helpful to the dementia sufferer practicing recognition and recall tasks, perhaps with the aid of another person such as a caregiver.

The method flow then returns to a determination of whether a subsequent real-time recognition task is desired to be performed, as shown at 312 and 302. Accordingly, for example, the Display Module 240 may again display the graphical user interface window 400 of FIG. 4, which displays the user selectable button 402 for again performing an image recognition task.

If it is determined at 302 that the user does not wish to perform real time image recognition, for example in response to the user's selection of and activities button 404 displayed by the Display Module 240, e.g., as shown in graphical user interface window 400 of FIG. 4, then the Display Module 240 displays a graphical user interface window 900 with user selectable buttons 902, 904, 906, 908 for selecting different therapy tasks and it is determined whether a therapy has been selected, as shown at 314.

Figure 10:
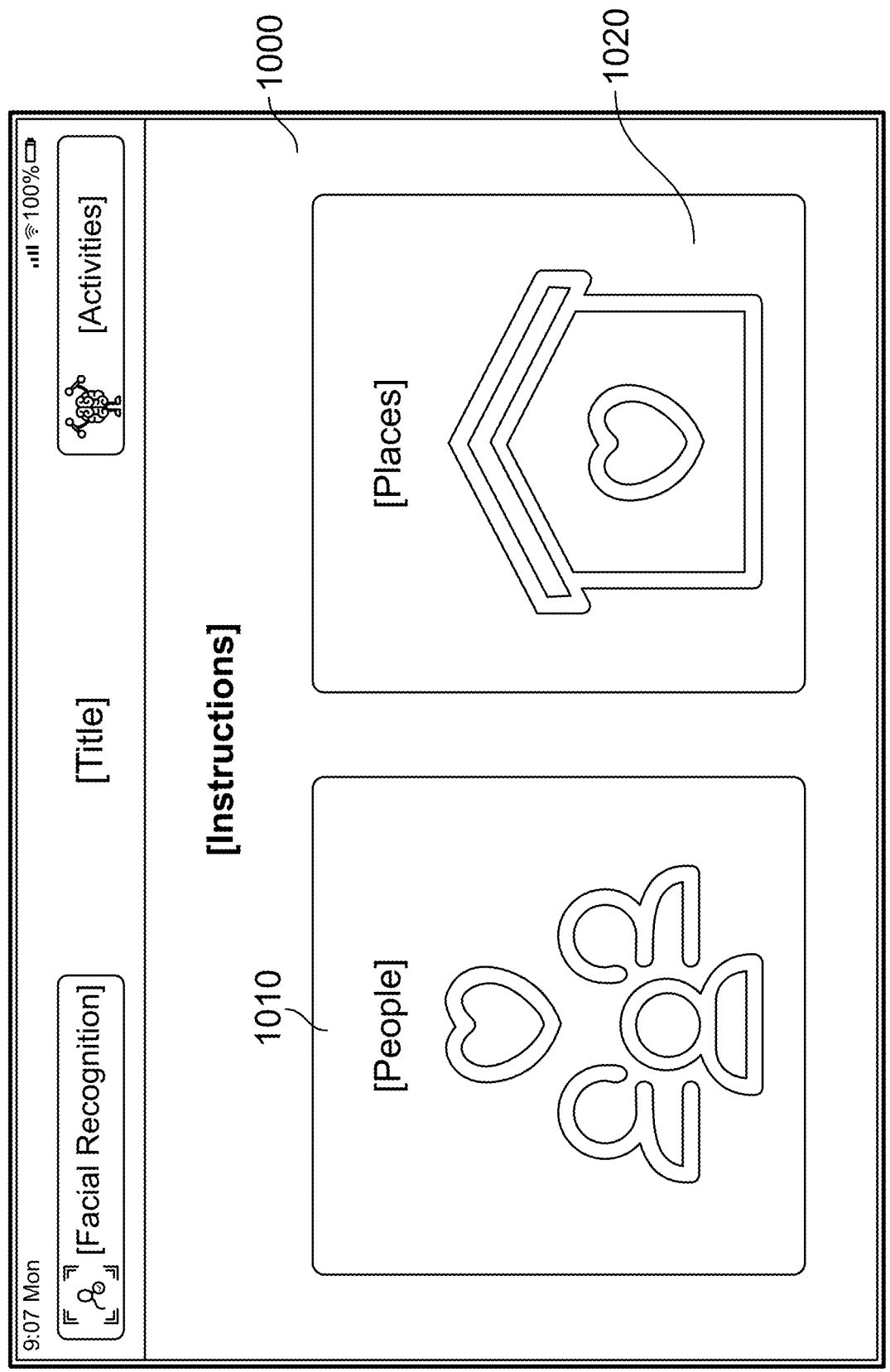
Figure 11:
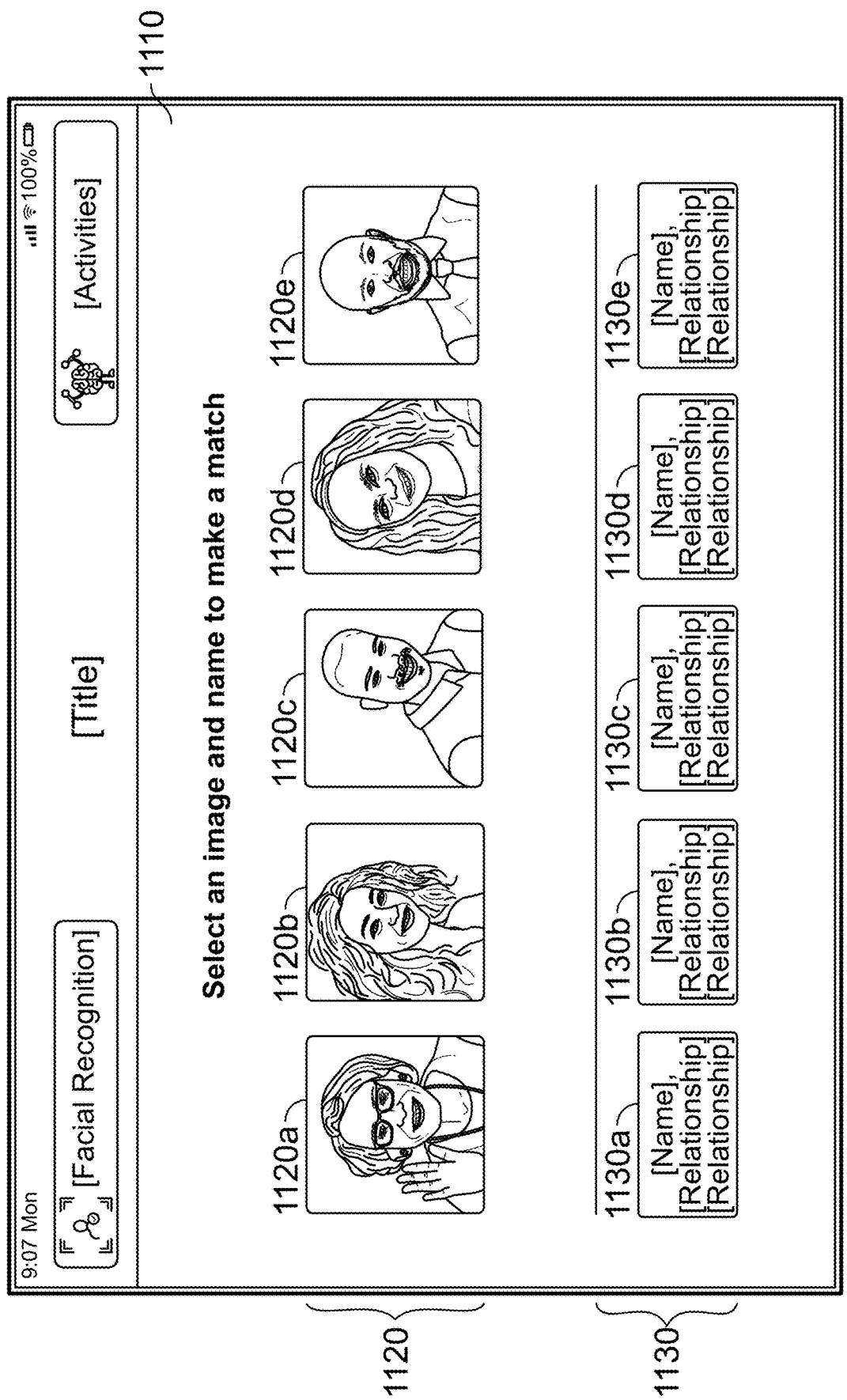

In response to the user's selection of one of those buttons, such as the Matching activity button 902, the Display Module 240 displays a graphical user interface window 1000 displaying user selectable buttons 1010, 1020 for performing an activity in relation to images of people or alternatively, images of places, respectively, as shown in FIG. 10. In response to the user selection of one of those buttons, such as the people button 1010, it is determined that a Therapy activity has been selected, as shown at 314. In either case, the Therapy Module 290 retrieves activity data for the selected therapy, as shown at 316. In this example, the Therapy Module 290 may retrieve from the Activity Data 224f instructions for displaying user interface windows corresponding to the Matching activity, along with an indication that, in this example, 5 subject images and related data associated with those 5 subject images, will be required for the Matching activity.

The Therapy Module 290 then retrieved Performance Data 224e, as shown at 318. The Performance Data indicate recognition failures or difficulties, as reflected by performance data stored by the IPM 250, e.g., as the result of use of the ARMBD 200 to recognize known subjects. For example, the Performance Data 224e may indicate that the ARMBD 200 has been used, or recently used, or frequently used, according to any suitable thresholds, to recognize a subject of "Jane."

The Therapy Module 290 then configures the selected therapy task, in this example the Matching activity, as a function of the retrieved Performance Data, as shown at 320. For example, the Therapy Module 290 may configure the matching activity to include display of at least one image of subject "Jane," along with images of other subjects, which may be selected in any suitable fashion, such as randomly.

Figure 12:
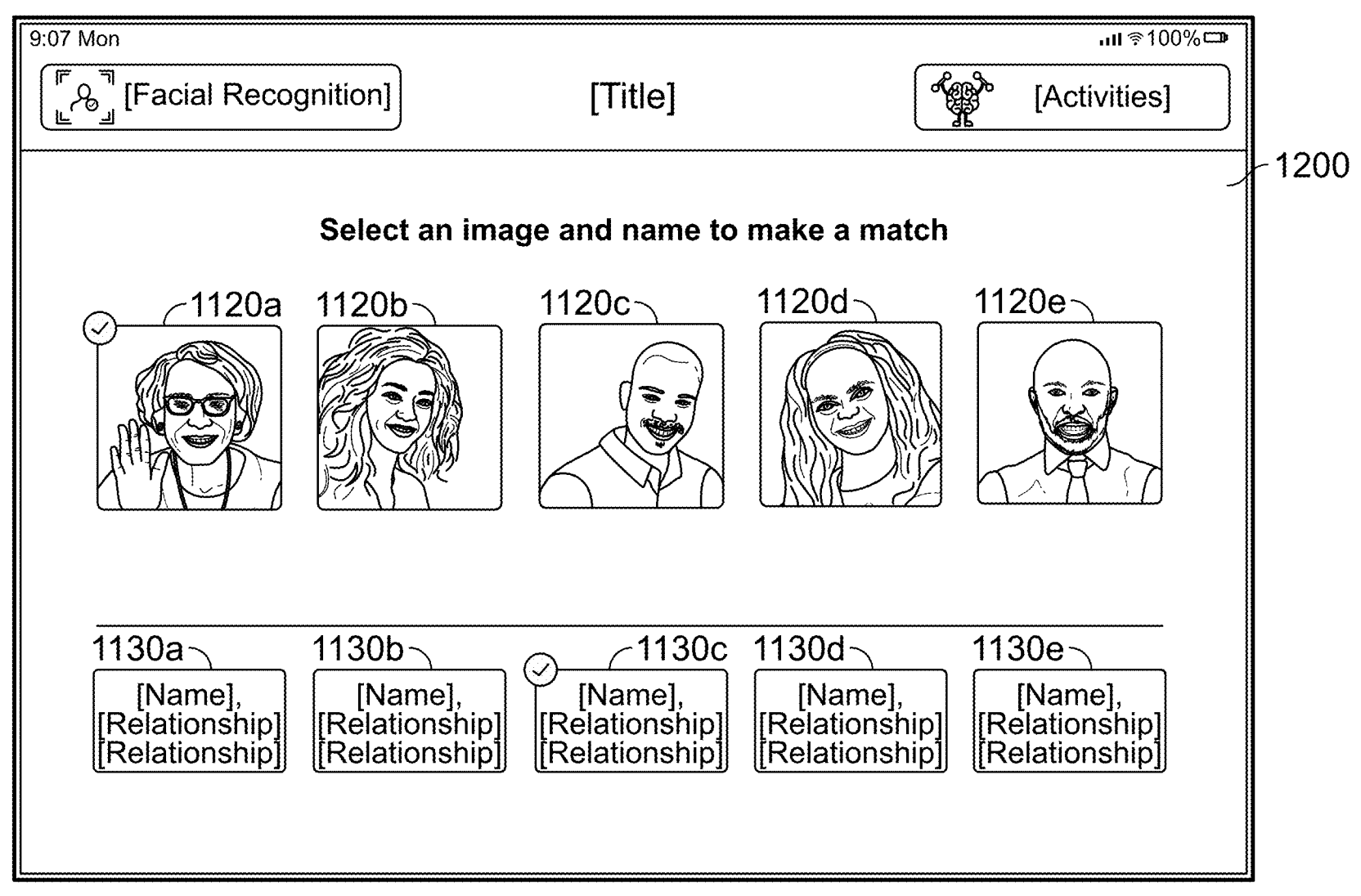
Figure 13:
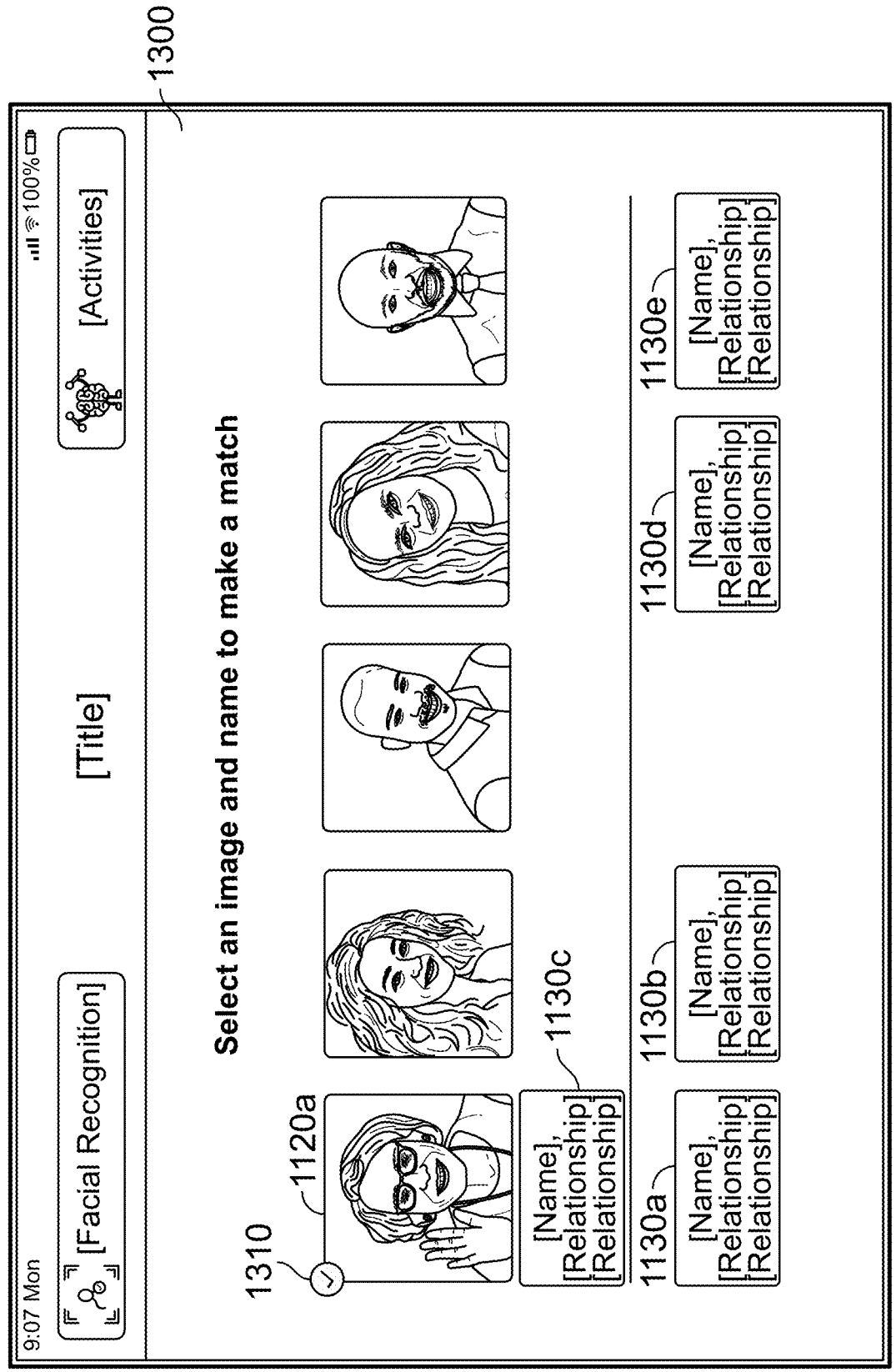
Figure 14:
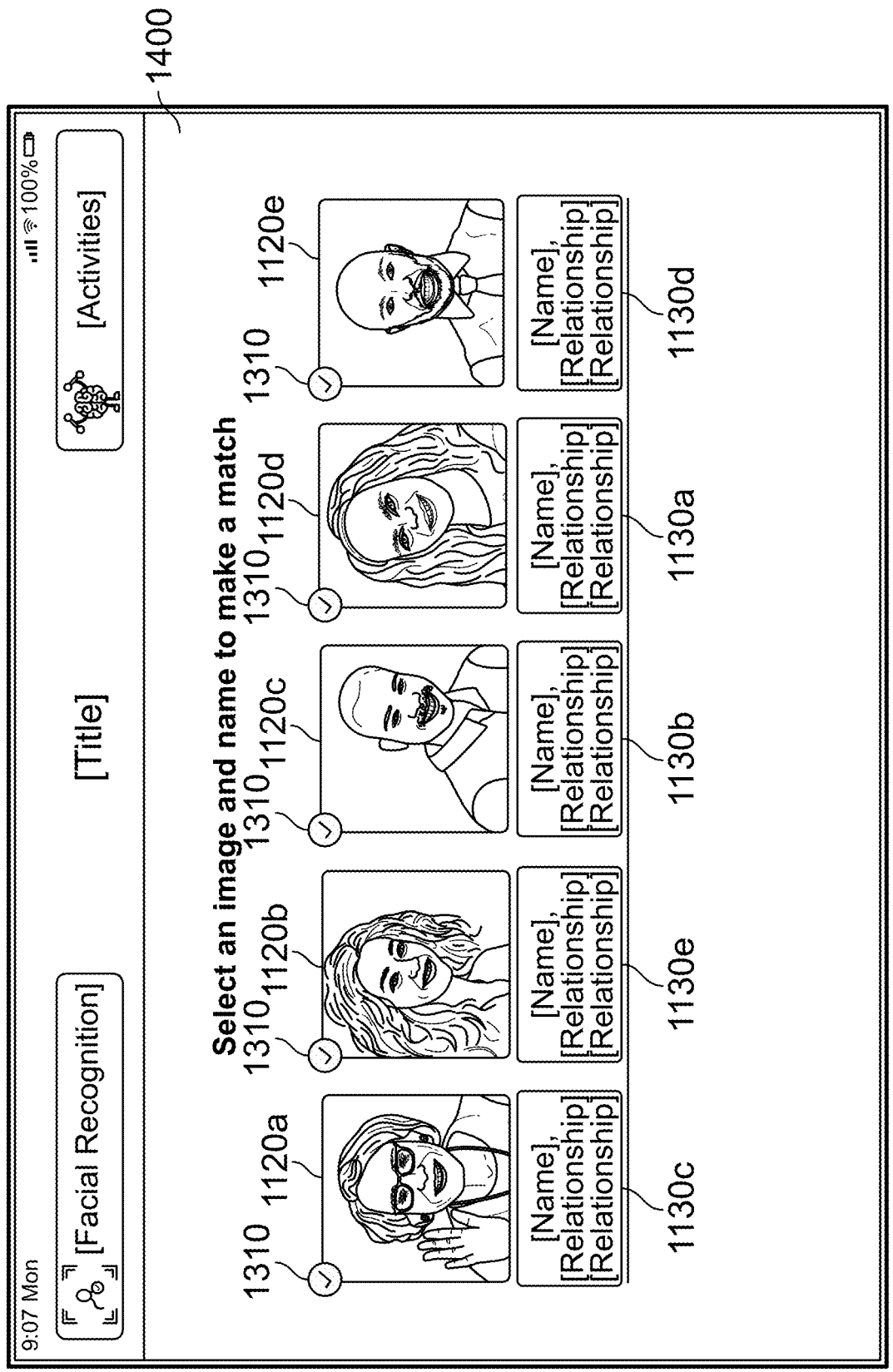
Figure 15:
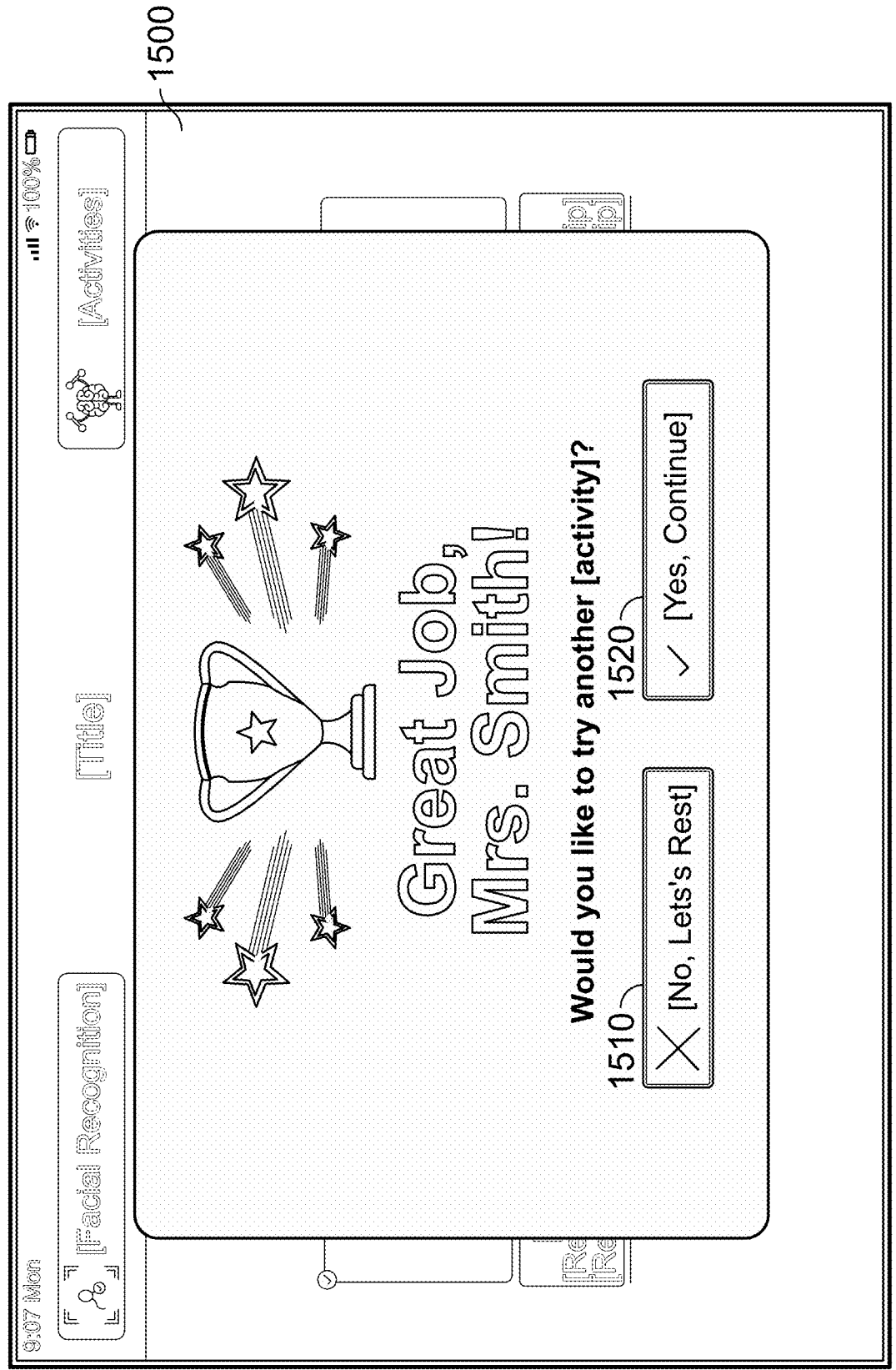
Figure 16:
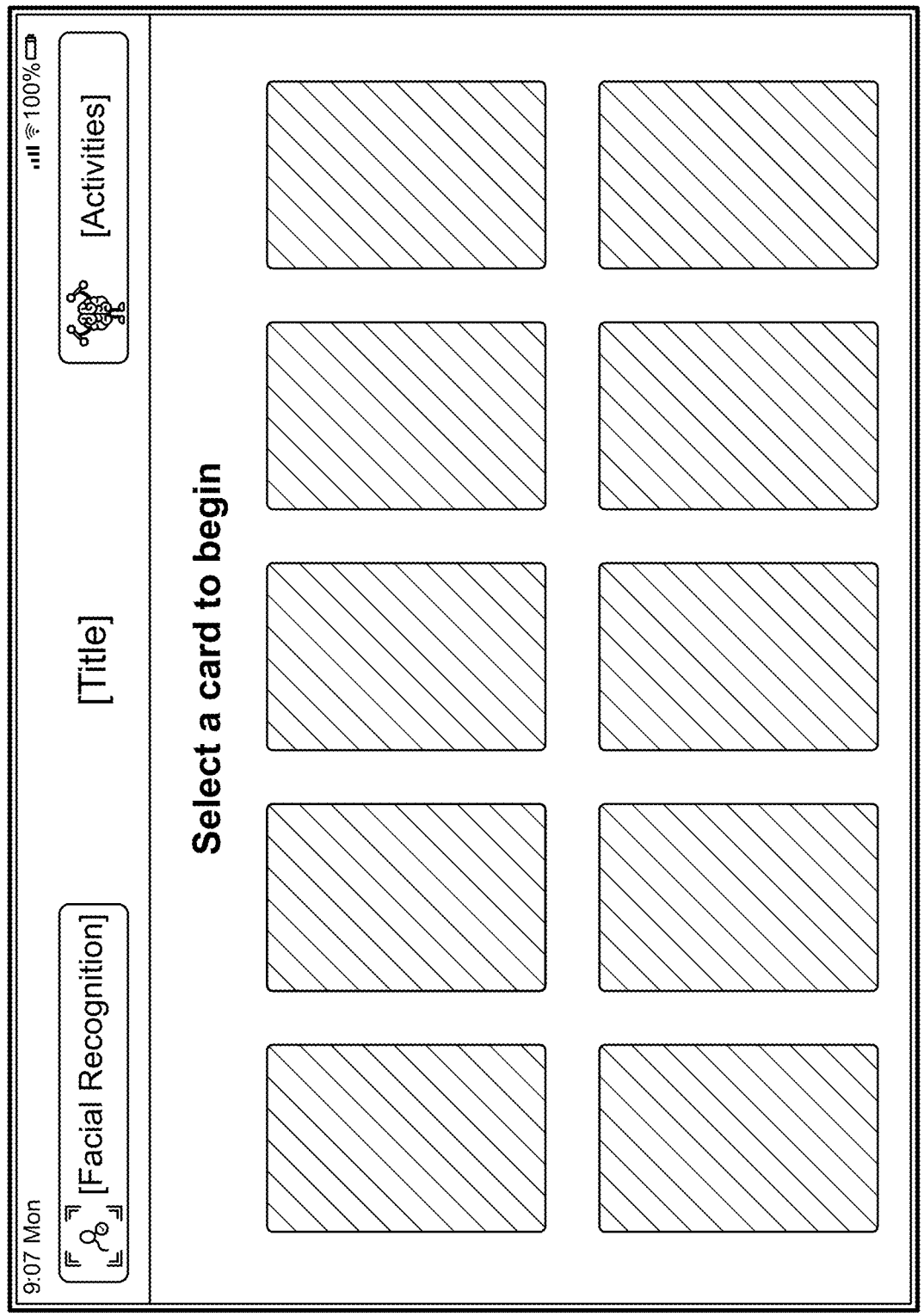
Figure 17:
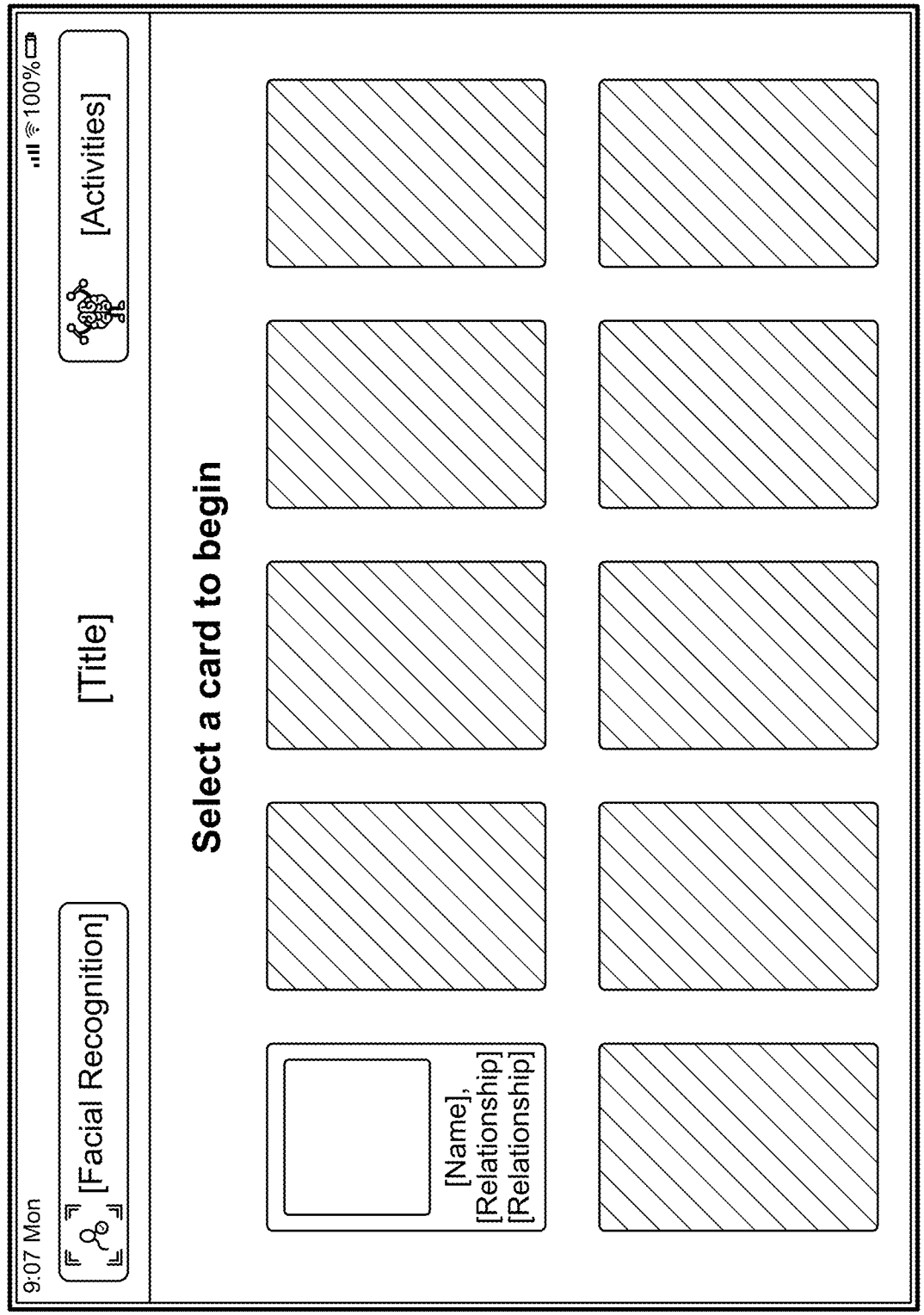
Figure 18:
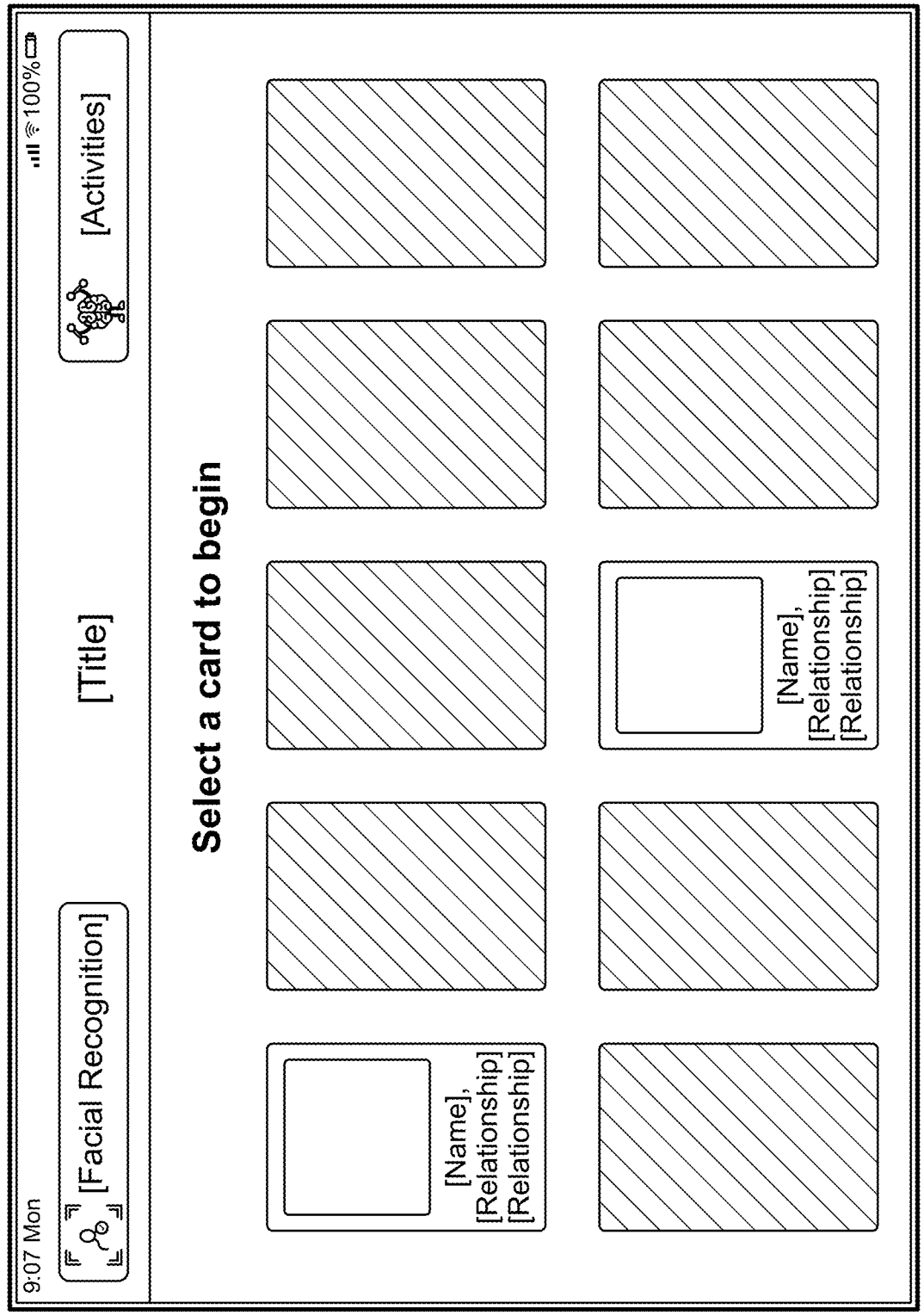
Figure 19:
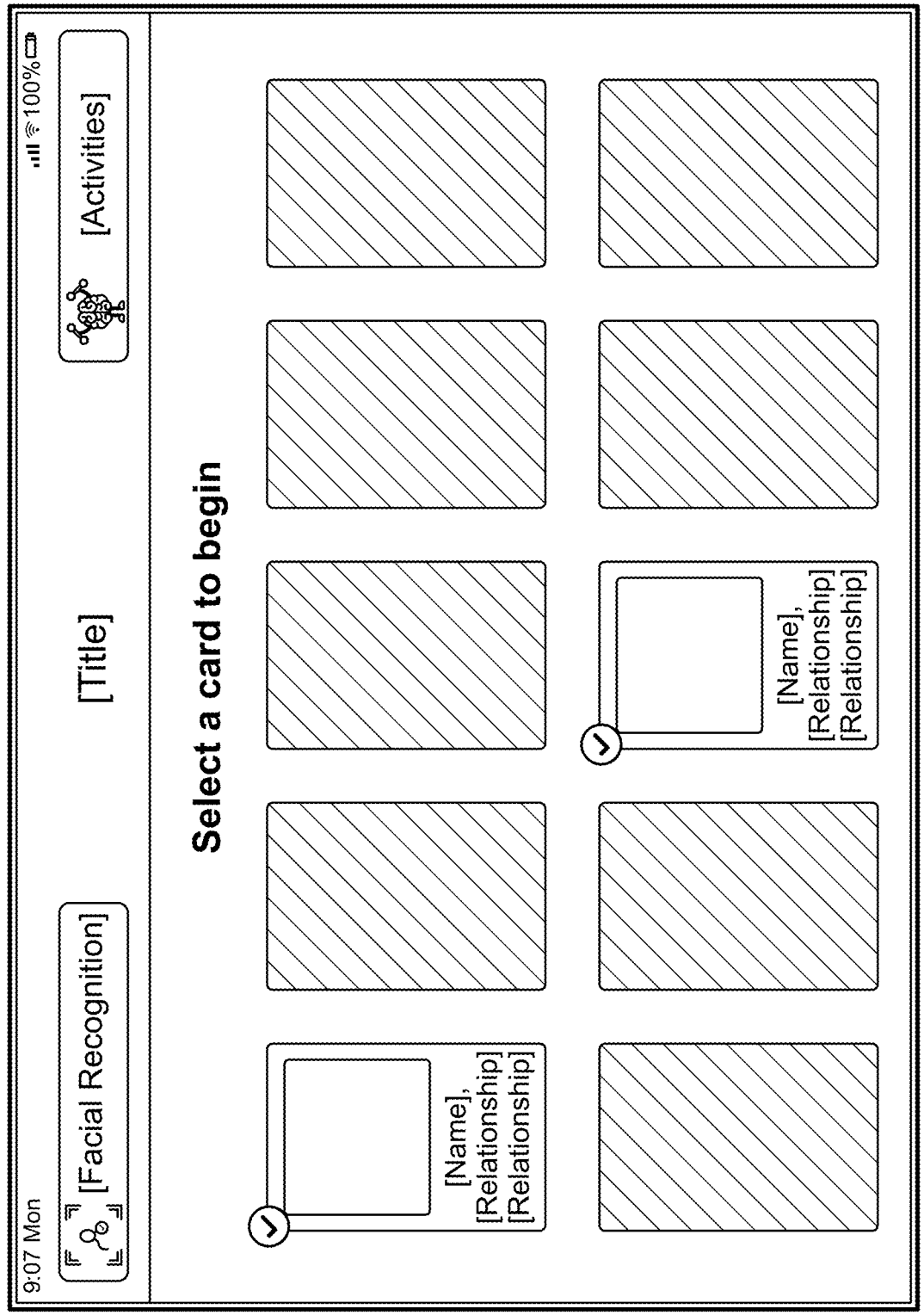
Figure 20:
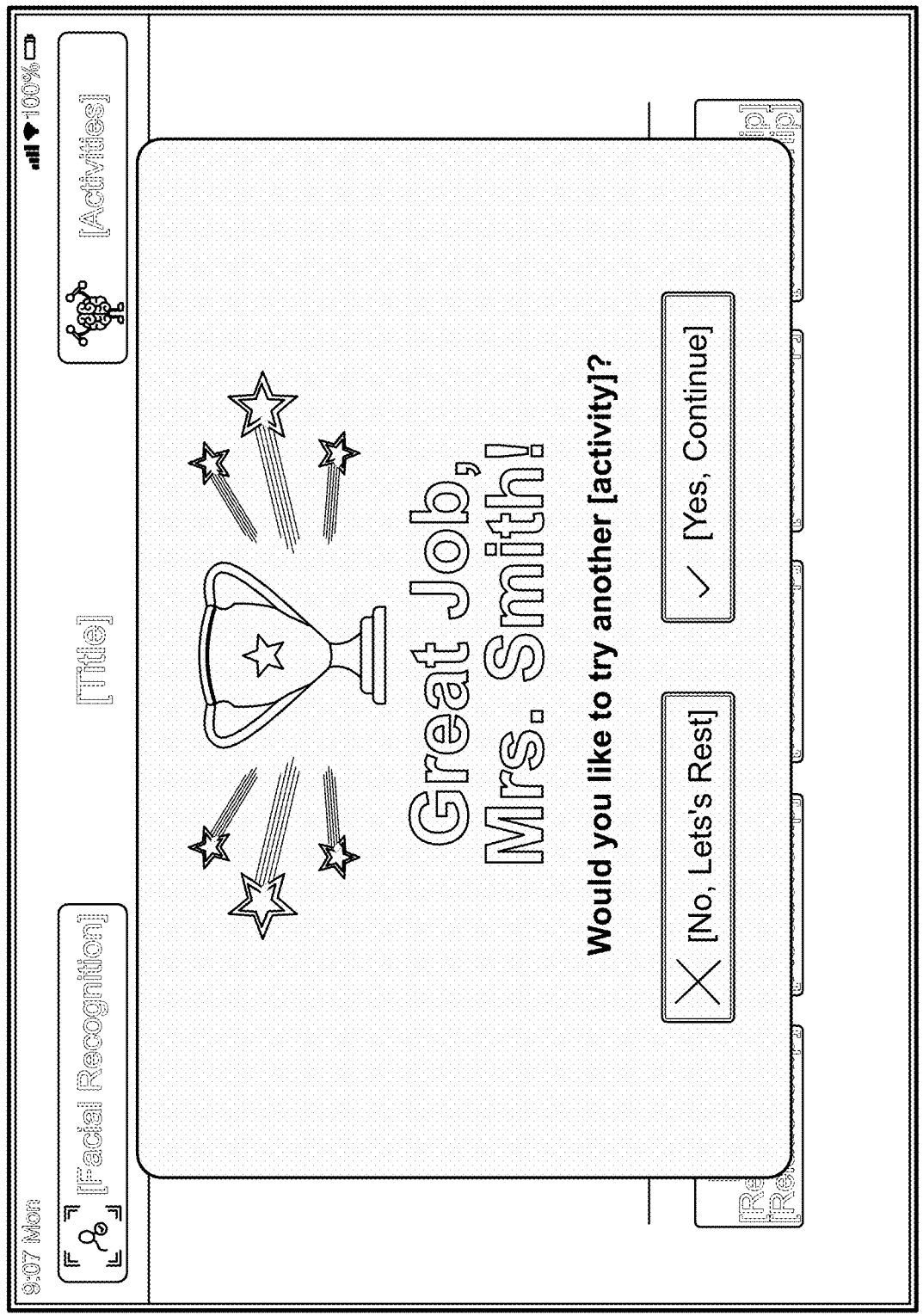

The Therapy Module 290 then causes display of the selected therapy activity, as shown at 322, which in this example is the Matching activity. Accordingly, in this example, the Therapy Module 290 displays a graphical user interface window 1110 for a matching-type therapy activity. In this activity, a plurality of images 1120a, 1120b, 1120c, 1120d, 1120e of persons known to the user are displayed in a first array 1120, and a plurality of tiles 1130a, 1130b, 1130c, 1130d, 1130e display associated contextual information associated with each of the persons known to the user are displayed in a second array 1130, and the user is tasked with selecting a respective tile with contextual information corresponding to each image. FIG. 12 shows a graphical user interface window 1200 indicating that the user has correctly matched an image 1120*a*, with a respective tile 1130*c*, having associated contextual information, and thus has properly recognized the subject. FIG. 13 shows a graphical user interface window 1300 displaying an icon 1310 indicating a correct match for image 1120*a*, with the matching contextual information tile 1130*c* moved into proximity with image 1120*a* to show the correct match and to prompt the user to perform a next match. FIG. 14 shows a graphical user interface window 1400 with icons 1310 indicating a correct match for each image 1120*a*, 1120*b*, 1120*c*, 1120*d*, 1120*e*. FIG. 15 displays a graphical user interface window 1500 displaying text confirming the successful completion of the activity, and user selectable buttons 1510, 1520 for ending the performance of therapy activities and for performing another therapy activity, respectively. These graphical user interface windows may be displayed by the Therapy Module 290.

It should be noted that in a preferred embodiment, the Monitoring Module 270 also tracks the user's performance during the therapy activities, and stores data as Performance Data 224*e* to indicate that there is difficulty and/or failed recognition with respect to certain subjects as a function of the user's performance and misidentifications or slow identifications in performance of the therapy activities.

It is next determined whether another therapy activity is desired, as shown at 324. This may be determined for example according to the user's selection of one of the user selectable buttons 1510, 1520 of the graphical user interface window 1500 of FIG. 15.

If it is determined that another therapy activity is desired, for example, as a result of selection of button 1520, then method flow returns to 314, where it is determined which therapy activity has been selected, and steps 314 to 324 may be repeated.

Any suitable therapy activities may be used, with therapy activities involving recall and recognition tasks designed to improve cognitive function being preferred. By way of additional example, FIGS. 16-20 show graphical user interface windows for a Concentration-type therapy activity that may be accessed by the user's selection of the Concentration button 904 displayed in the graphical user interface window 900 of FIG. 9. The therapy activity may proceed in a generally conventional manner characteristic of a concentration-type card game in which the user may select pairs of displayed tiles in an attempt to match subject images, tiles of related information, or a subject image with an associated tile of related information in a manner resembling a conventional concentration type card game. The subject images and related information content may be that of persons known to the user, and may be retrieved by the Therapy Module from Picture Data 224*c*, Related Data 224*d*, or from other storage such as storage at the IPADSS 150, as part of the configuration of the activity at 320. Again, the Performance Data 224*e* may be retrieved and used to configure the activity to involve use of subject images and/or related data associated with subjects that the dementia sufferer had difficulties in recognizing, as reflected in the Performance Data.

Figure 9:
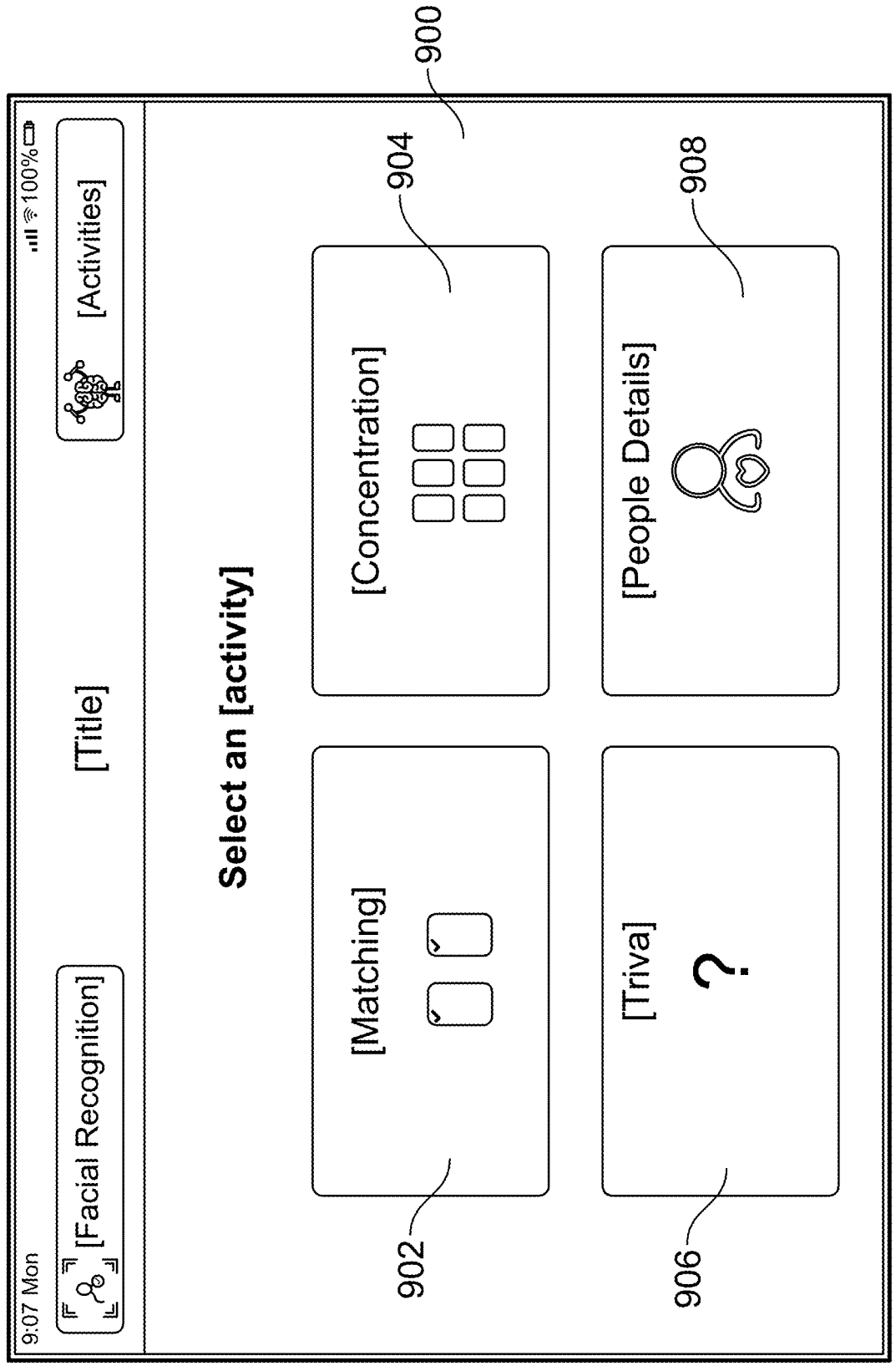
Figure 21:
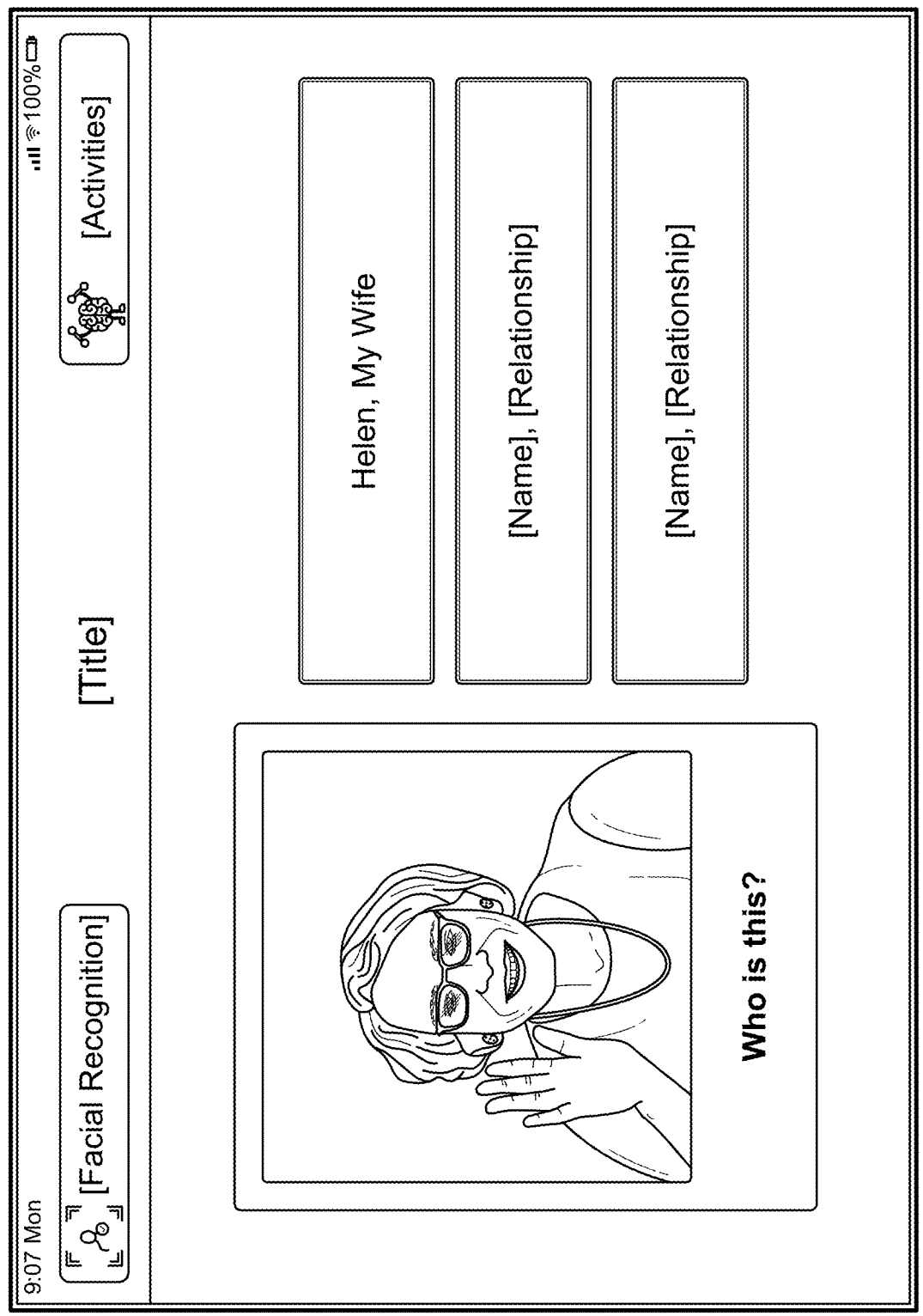
Figure 22:
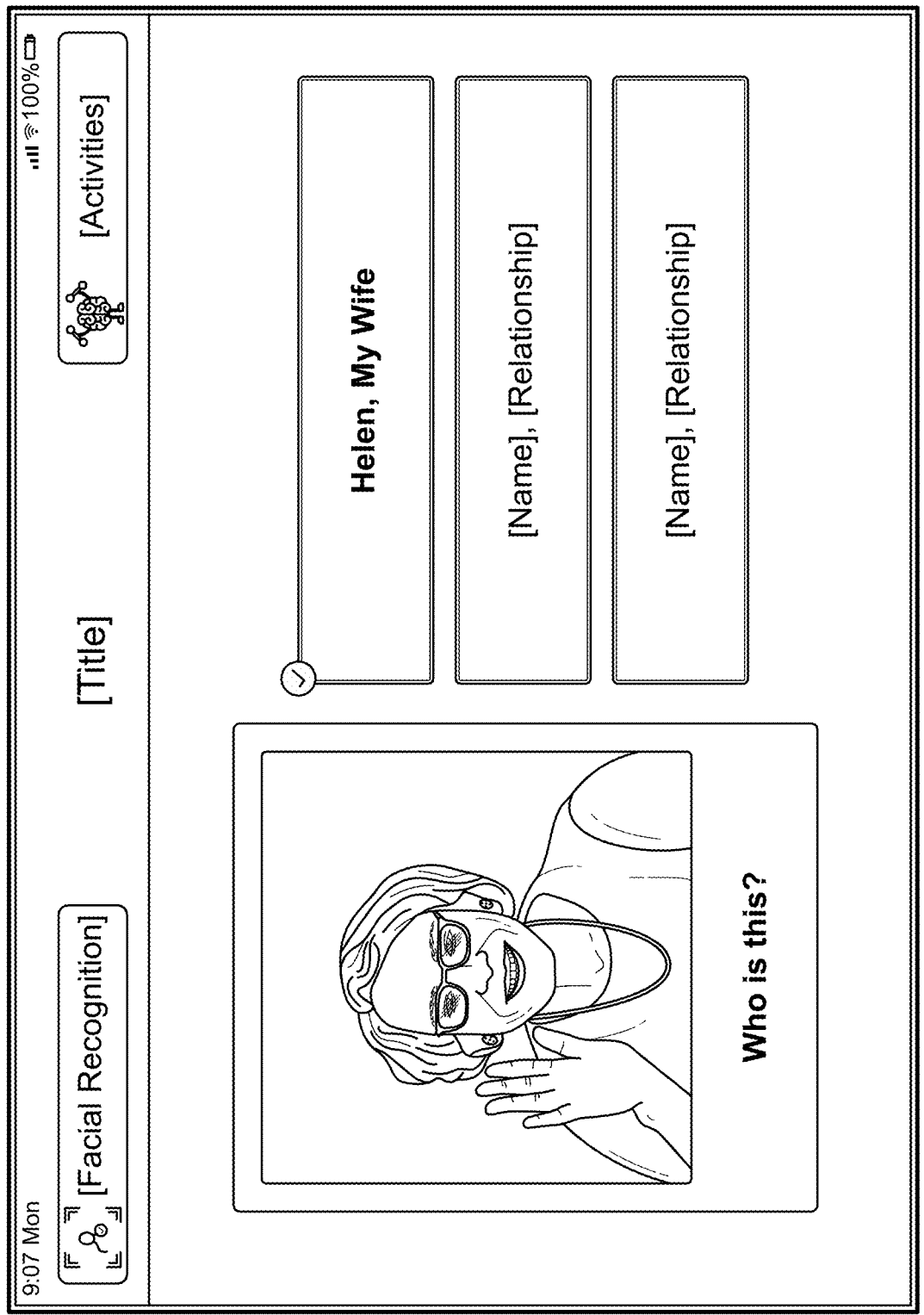
Figure 23:
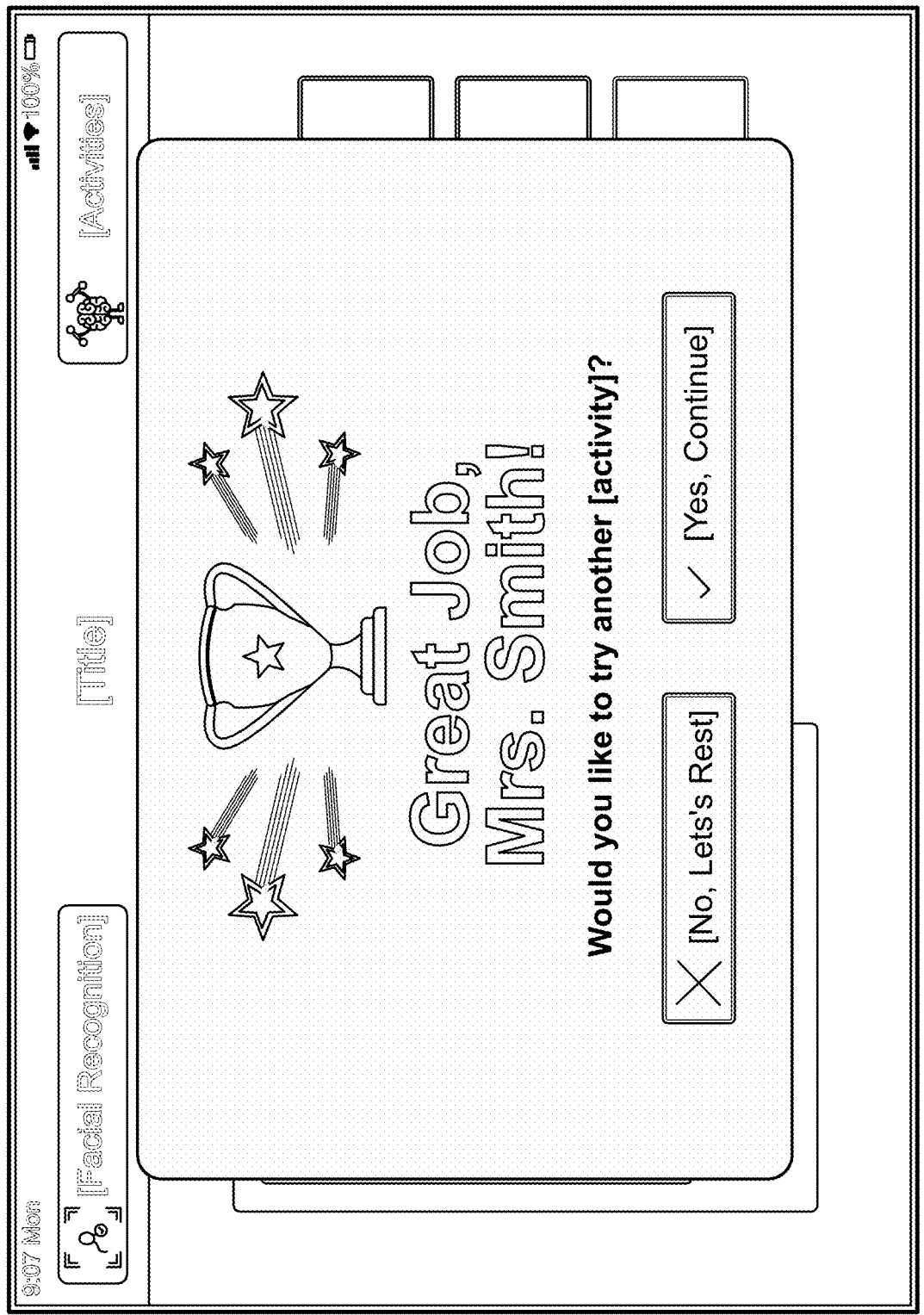

By way of additional example, FIGS. 21-23 show graphical user interface windows for a trivia-type therapy activity that may be accessed by the user's selection of the Trivia button 906 displayed in the graphical user interface window 900 of FIG. 9. The therapy activity may proceed in a generally conventional manner characteristic of a trivia-type card game in which a subject image may be displayed to the user along with a plurality of user-selected tiles containing information, only one of which may contain information that is accurate, such that the user is challenged to select a tile from the group of tiles that includes information properly associated with the subject shown in the image. The subject images and related information content may be that of persons known to the user, and may be retrieved by the Therapy Module from Picture Data 224*c*, Related Data 224*d*, or from other storage such as storage at the IPADSS 150, as part of the configuration of the activity at 320. Again, the Performance Data 224*e* may be retrieved and used to configure the activity to involve use of subject images and/or related data associated with subjects that the dementia sufferer had difficulties in recognizing, as reflected in the Performance Data.

Figure 24:
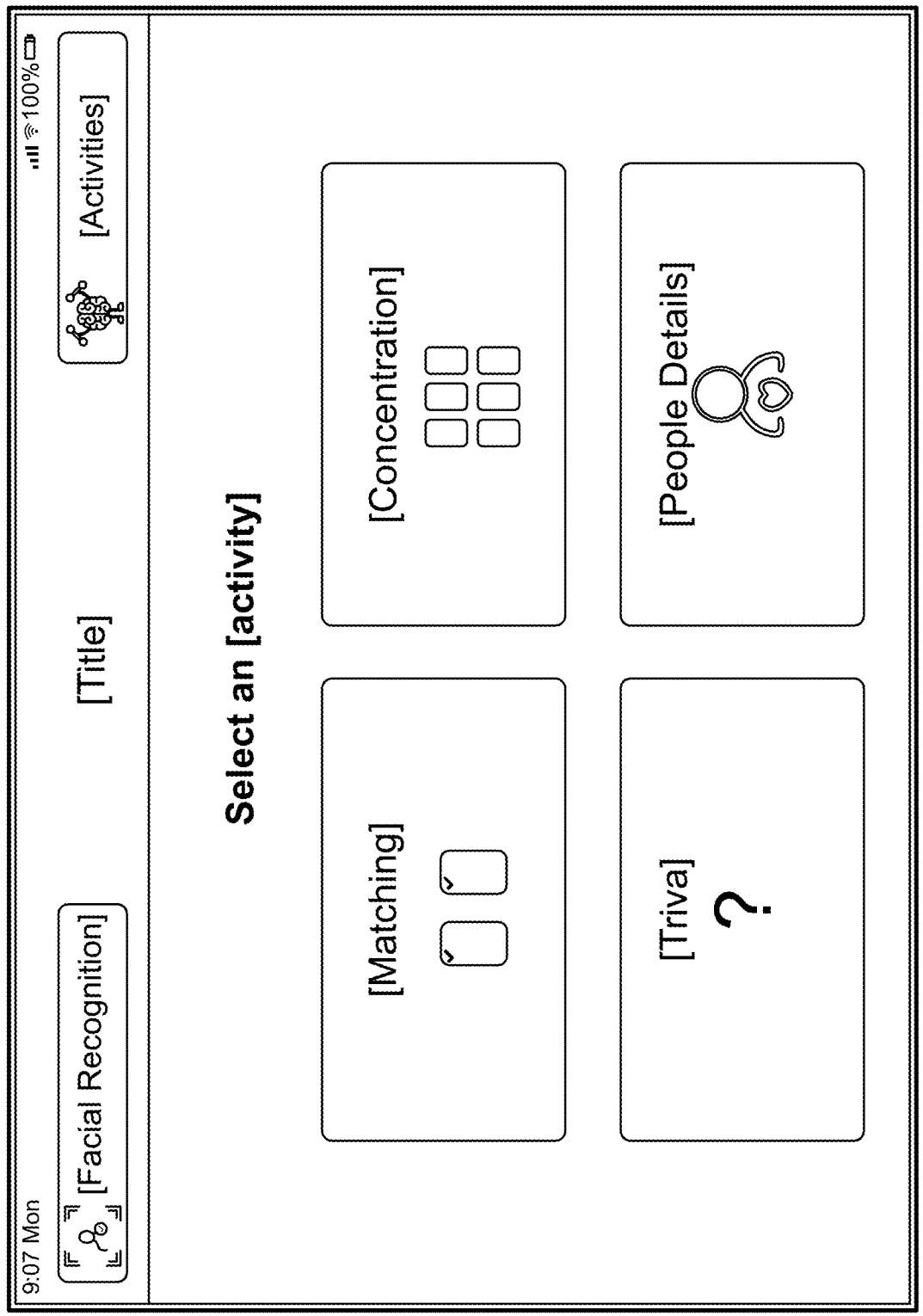
Figure 25:
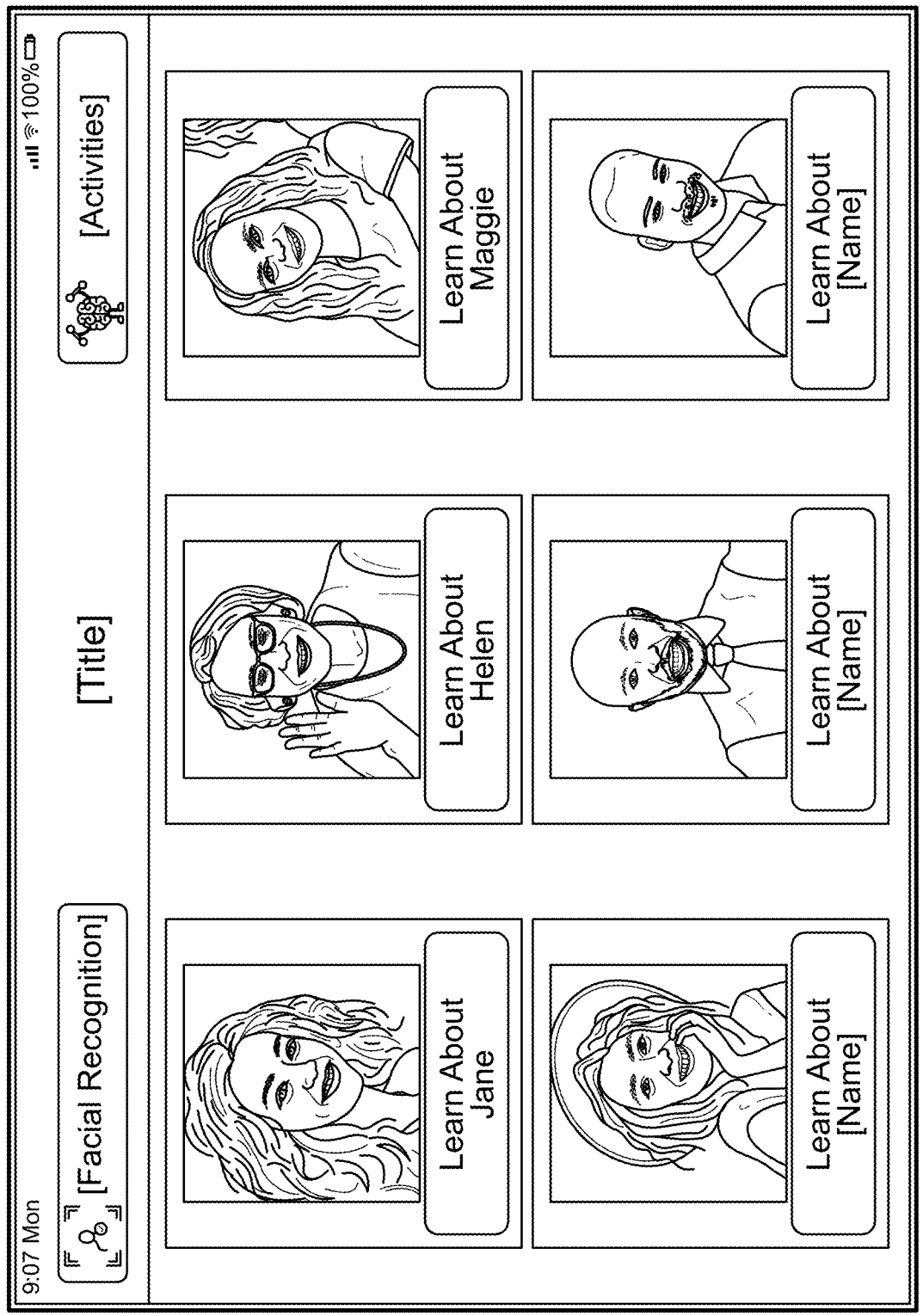

By way of additional example, FIGS. 24-25 show graphical user interface windows for a People Details-type therapy activity that may be accessed by the user's selection of the People Details button 908 displayed in the graphical user interface window 900 of FIG. 9. The therapy activity may involve display of a plurality of images of subjects known to the user, along with user selectable buttons for causing display of additional images of the same subject at the one associated with the user selected button, and or related information, in a task similar to that of the reminiscence task described above in relation to the Reminiscence Module 280, and result in display of a graphical user interface window similar to that of FIG. 8. The subject images and related information content may be that of persons known to the user, and may be retrieved by the Therapy Module from Picture Data 224*c*, Related Data 224*d*, or from other storage such as storage at the IPADSS 150, as part of the configuration of the activity at 320. Again, the Performance Data 224*e* may be retrieved and used to configure the activity to involve use of subject images and/or related data associated with subjects that the dementia sufferer had difficulties in recognizing, as reflected in the Performance Data.

If it is determined at 324 that the user does not wish to perform another therapy activity, e.g., as a result of the user's selection of user selectable button 1510 of FIG. 15 or a similar button, then method flow returns to 302, where it is again determined whether the user wishes to perform real time image recognition, and the method continues as described above.

It should be noted that the app/device 200 and/or the IPADSS 150 may be used to track data, and provide reporting functionality via the app/device 200 or otherwise, e.g., to caregivers. By way of example, analytics-type data may be captured to reflect when certain therapies are used, how often, success rates, etc., when people are not identified during certain therapy activities and other difficulties in identifying people, which may be used to determine what therapies to provide via a graphical user interface display of the device, how to configure them, how often to provide them, and for general reporting/caregiver feedback purposes.

Accordingly, it will be appreciated that the present invention provides a computerized system and method for user interface management that provides an augmented reality-based experience that delivers real-time visual cues to a cognitively impaired person. More particularly, the system uses image/facial recognition to identify persons/places/objects encountered by a person/dementia sufferer and captured by a camera of a computing device, retrieves information associated with identified person/place/object, and displays retrieved information associated with identified person/place/object to the person/dementia sufferer via the device, e.g., in an augmented reality overlay to an image captured by the camera. The information may identify the identified person's relationship with dementia sufferer and other pertinent details. Accordingly, for example, a person with cognitive impairment can quickly assess who is approaching them, based on facial recognition.

Further, the present invention provides a computerized system and method for user interface management that provides an augmented reality-based experience that monitors a user's visual recognition performance, and that provides visual recognition training based on observed visual recognition performance. More particularly, system may apply machine learning to identify a frequency in which a user needs assistance to identify an individual and/or their relationship to that person, and customize therapeutic exercises, digitally, specific to each user's needs. For example, if a user needs recognition assistance with person X more frequently, recognition exercises specific to person X will be pushed to the user in the form of identifying images of that person at varying ages, in various settings, or dress.

The various implementations and examples shown above illustrate a method and system for user interface management that provides an augmented reality-based experience that delivers real-time visual cues to a cognitively impaired person. using an electronic device. However, the device could be used in contexts other than for cognitively impaired persons, e.g., where recognition and/or situational awareness is needed such as learning names for objects and what they mean to a user, learning in another language, or learning a new skill, as an instructional aid. As is evident from the foregoing description, certain aspects of the present implementation are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present implementation. Accordingly, the specification and drawings are to be regarded in an illustrative rather than a restrictive sense.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

In an exemplary embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a smart phone, a web appliance, a network router, switch or bridge, or any machine capable of executing a set of instructions (sequential or otherwise) that specify actions to be taken by that machine or computing device. Further, while only a single machine is illustrated, the term "machine" shall also be taken to include any collection of machines that individually or jointly execute a set (or multiple sets) of instructions to perform any one or more of the methodologies discussed herein.

The example computer system and client computers include a processor (e.g., a central processing unit (CPU), a graphics processing unit (GPU) or both), a main memory and a static memory, which communicate with each other via a bus. The computer system may further include a video/graphical display unit (e.g., a liquid crystal display (LCD) or a cathode ray tube (CRT)). The computer system and client computing devices also include an alphanumeric input device (e.g., a keyboard or touch-screen), a cursor control device (e.g., a mouse or gestures on a touch-screen), a drive unit, a signal generation device (e.g., a speaker and microphone) and a network interface device.

The system may include a computer-readable medium on which is stored one or more sets of instructions (e.g., software) embodying any one or more of the methodologies or systems described herein. The software may also reside, completely or at least partially, within the main memory and/or within the processor during execution thereof by the computer system, the main memory and the processor also constituting computer-readable media. The software may further be transmitted or received over a network via the network interface device.

The term "computer-readable medium" should be taken to include a single medium or multiple media (e.g., a centralized or distributed database, and/or associated caches and servers) that stores the one or more sets of instructions. The term "computer-readable medium" shall also be taken to include any medium that is capable of storing or encoding a set of instructions for execution by the machine and that cause the machine to perform any one or more of the methodologies of the present implementation. The term "computer-readable medium" shall accordingly be taken to include, but not be limited to, solid-state memories, and optical media, and magnetic media.

The present invention may be operational with numerous other general-purpose or special-purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, cellular telephones, network PCs, minicomputers, mainframe computers, distributed computing environments that include any of the above-mentioned systems or devices, and the like.

The present invention has been described in the general context of computer-executable instructions, such as program modules or engines, being executed by a computer. Generally, program modules/engines include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules/engines may be located in local and/or remote computer-storage media including, by way of example only, memory storage devices.

The exemplary computing system may include general-purpose computing hardware in the form of a server. Components of the server may include, without limitation, a processing unit, internal system memory, and a suitable system bus for coupling various system components, including a database cluster, with the server. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

The server typically includes therein, or has access to, a variety of computer-readable media, for instance, via a database cluster. Computer-readable media can be any available media that may be accessed by the server, and includes volatile and nonvolatile media, as well as removable and non-removable media. By way of example, and not limitation, computer-readable media may include computer-storage media and communication media. Computer-storage media may include, without limitation, volatile and non-volatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information, and which may be accessed by the server. Communication media typically embodies computer readable instructions, data structures, program modules, or other data in a modulated data signal, such as a carrier wave or other transport mechanism, and may include any information delivery media. The term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The server may operate in a computer network using logical connections to one or more remote computers. Remote computers may be located at a variety of locations or over the Internet. The remote computers may be personal computers, servers, routers, network PCs, peer devices, other common network nodes, or the like, and may include some or all of the elements described above in relation to the server. The computing devices can be personal digital assistants or other like devices.

Exemplary computer networks may include, without limitation, local area networks (LANs) and/or wide area networks (WANs). Such networking environments are commonplace in offices, enterprise-wide computer networks, intranets, and the Internet. When utilized in a WAN networking environment, the server may include a modem/network card or other means for establishing communications over the WAN, such as the Internet. In a networked environment, program modules or portions thereof may be stored in the server, in the database cluster, or on any of the remote computers. For example, and not by way of limitation, various application programs may reside on the memory associated with any one or more of the remote computers. It will be appreciated by those of ordinary skill in the art that the network connections shown are exemplary and other means of establishing a communications link between the computers (e.g., the server and remote computers) may be utilized.

In operation, a user may enter commands and information into the server or convey the commands and information to the server via one or more of the remote computers through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote device to the server. In addition to a monitor, the server and/or remote computers may include other peripheral output devices, such as speakers and a printer.

Many other internal components of the server and the remote computers/computing devices are not shown because such components and their interconnection are well known. Accordingly, additional details concerning the internal construction of the server and the remote computers/computing devices are not further disclosed herein.

Although methods and systems of embodiments of the present invention may be implemented in a WINDOWS or LINUX operating system, operating in conjunction with an Internet-based delivery system, one of ordinary skill in the art will recognize that the described methods and systems can be implemented in any system supporting the functionality described herein. As contemplated by the language above, the methods and systems of embodiments of the present invention may also be implemented on a stand-alone desktop, personal computer, cellular phone, smart phone, tablet, PDA, or any other computing device used in various locations.

Additionally, computer readable media storing computer readable code for carrying out the method steps identified above is provided. The computer readable media stores code for carrying out subprocesses for carrying out the methods described herein.

A computer program product recorded on a computer readable medium for carrying out the method steps identified herein is provided. The computer program product comprises computer readable means for carrying out the methods described above.

While there have been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

What is claimed is:

1. An augmented reality-based monitoring device comprising:
   a display device;
   a user input device;
   a memory comprising a non-transitory data processor-readable medium;

an imaging device operatively connected to said memory;

a data processor operatively connected to said memory, said display device, said imaging device, and said user input device;

user interface management instructions embodied in data processor-executable code stored in the memory, said user interface management instructions being executable by the data processor to provide a user interface management engine configured to:

capture at least one image via said imaging device and store data representative of said at least one image in said memory;

transmit data representing said image to perform an image processing function for recognition of a subject of said image;

if said subject is determined to match a previously stored image, then:
retrieve related data associated with said previously stored image; and
display said related data via said display device; and if said subject is determined not to match a previously stored image, then:
retrieve at least one previously stored image;
retrieve related data associated with said at least one previously stored image; and
display said at least one previously stored image in association with said related data via said display device; and store in said memory data reflecting use of said imaging device to identify said subject.

2. The augmented reality-based monitoring device of claim 1, wherein said user interface management instructions further comprise instructions executable by the data processor to configure the user interface management engine to:
identify a plurality of faces within a displayed image; and
identify a most prominent face from among said plurality of faces.

3. The augmented reality-based monitoring device of claim 2, wherein said user interface management instructions are configured to identify a most prominent face from among said plurality of faces by calculating at least one dimension of the plurality of faces and comparing calculated dimensions for the plurality of faces to determine which face has a largest dimension.

4. The augmented reality-based monitoring device of claim 2, wherein said user interface management instructions further comprise instructions executable by the data processor to configure the user interface management engine to:
display via said display device visible indicia identifying said most prominent face within said displayed image.

5. The augmented reality-based monitoring device of claim 3, wherein said user interface management instructions are configured to display via said display device visible indicia identifying said most prominent face as an overlay graphic superimposed over a displayed image.

6. The augmented reality-based monitoring device of claim 2, wherein said user interface management instructions to:
transmit data representing said image to perform the image processing function for recognition of the most prominent face as the subject of said image.

7. The augmented reality-based monitoring device of claim 1, wherein said user interface management instructions further comprise instructions executable by the data processor to configure the user interface management engine to:
retrieve from said memory activity data for a selected therapy;
retrieve from said memory said data reflecting use of said imaging device to identify said subject;
retrieve at least one of text and an image related to said subject;
retrieve from said memory said data reflecting use of said imaging device to identify at least one additional subject;
retrieve at least one of text and an image related to said at least one additional subject;
configure said selected therapy as a function of said data reflecting use of said imaging device to identify said at least one subject to include display said at least one of text and an image related to each said subject and said at least one additional subject; and
display via said display device said at least one of text and an image related to said subject and said at least one additional subject as part of displaying of said selected therapy.

8. The augmented reality-based monitoring device of claim 1, wherein said user interface management instructions comprise instructions executable by the data processor to configure the user interface management engine to configure said selected therapy as a function of said data reflecting use of said imaging device to identify said at least one subject comprises instructions to:
select images of at least one additional subject randomly from among a plurality of subjects for which there is associated stored data.

9. The augmented reality-based monitoring device of claim 1, wherein said user interface management instructions comprise instructions executable by the data processor to display via said display device said at least one of text and an image related to said subject and said at least one additional subject as part of displaying of said selected therapy comprises instructions to:
provide displays providing one of a matching-type therapy activity, a concentration-type therapy activity, a trivia-type therapy activity, and a people details-type therapy activity.

10. The augmented reality-based monitoring device of claim 2, wherein said user interface management instructions further comprise instructions executable by the data processor to configure the user interface management engine to:
track usage data and determine analytics-type data indicating at least one of when each therapy activity is used, how often each therapy activity is used, success rates for each therapy activity, people that are not identified successfully in each therapy activity; and
report results by one of displaying data via the augmented reality-based monitoring device and transmitting data via a network to an external computing device.

11. A computer-implemented method of controlling a display of a computerized device to provide an augmented reality-based therapeutic experience, the computerized device comprising a memory operatively comprising a non-transitory data processor-readable medium, a data processor operative connected to the memory, the display and the user input component, and user interface management instructions embodied in data processor-executable code stored in the memory and executable by the data processor, the method comprising:

capturing at least one image via said imaging device and store data representative of said at least one image in said memory;

transmitting data representing said image to perform an image processing function for recognition of a subject of said image;

if said subject is determined to match a previously stored image, then:
retrieving related data associated with said previously stored image; and
displaying said related data via said a display device; and if said subject is determined not to match a previously stored image, then:
retrieving at least one previously stored image;
retrieving related data associated with said at least one previously stored image; and
displaying said at least one previously stored image in associated with said related data via said display device; and storing in said memory data reflecting use of said imaging device to identify said subject.

12. The method of claim 11, further comprising:
identifying a plurality of faces within a displayed image; and
identifying a most prominent face from among said plurality of faces.

13. The method of claim 12, further comprising:
identifying a most prominent face from among said plurality of faces by calculating at least one dimension of the plurality of faces and comparing calculated dimensions for the plurality of faces to determine which face has a largest dimension.

14. The method of claim 12, further comprising:
displaying via said display device visible indicia identifying said most prominent face within said displayed image.

15. The method of claim 13, further comprising:
displaying via said display device visible indicia identifying said most prominent face as an overlay graphic superimposed over a displayed image.

16. The method of claim 12, further comprising:
transmitting data representing said image to perform the image processing function for recognition of the most prominent face as the subject of said image.

17. The method of claim 11, further comprising:
retrieving from said memory activity data for a selected therapy;
retrieving from said memory said data reflecting use of said imaging device to identify said subject;
retrieving at least one of text and an image related to said subject;
retrieving from said memory said data reflecting use of said imaging device to identify at least one additional subject;
retrieving at least one of text and an image related to at least one additional subject;
configuring said selected therapy as a function of said data reflecting use of said imaging device to identify said at least one subject to include display said at least one of text and an image related to each said subject and said at least one additional subject; and
displaying via said display device said at least one of text and an image related to said subject and said at least one additional subject as part of displaying of said selected therapy.

18. The method of claim 11, wherein said configuring said selected therapy as a function of said data reflecting use of said imaging device to identify said at least one subject comprises:
selecting images of at least one additional subject randomly from among a plurality of subjects for which there is associated stored data.

19. The method of claim 11, further comprising:
providing displays providing one of a matching-type therapy activity, a concentration-type therapy activity, a trivia-type therapy activity, and a people details-type therapy activity.

20. The method of claim 12, further comprising:
tracking usage data and determine analytics-type data indicating at least one of when each therapy activity is used, how often each therapy activity is used, success rates for each therapy activity, people that are not identified successfully in each therapy activity; and
reporting results by one of displaying data via the augmented reality-based monitoring device and transmitting data via a network to an external computing device.

21. A computer program product for implementing a method of controlling a display of a computerized device, the computer program product comprising a non-transitory computer-readable medium storing executable instructions that, when executed by a processor, cause a computerized augmented reality-based monitoring device to perform a method comprising:
capturing at least one image via said imaging device and store data representative of said at least one image in said memory;
transmitting data representing said image to perform an image processing function for recognition of a subject of said image;
if said subject is determined to match a previously stored image, then:
retrieving related data associated with said previously stored image; and
displaying said related data via said a display device; and
if said subject is determined not to match a previously stored image, then:
retrieving at least one previously stored image;
retrieving related data associated with said at least one previously stored image; and
displaying said at least one previously stored image in associated with said related data via said display device; and
storing in said memory data reflecting use of said imaging device to identify said subject.

* * * * *